US 6,982,087 B2
Jan. 3, 2006

(12) United States Patent
Johnston et al.

(10) Patent No.: US 6,982,087 B2
(45) Date of Patent: Jan. 3, 2006

(54) VECTORS DERIVED FROM SOUTH AFRICAN ARBOVIRUS NO. 86

(75) Inventors: Robert E. Johnston, Chapel Hill, NC (US); Mark T. Heise, Durham, NC (US); Dennis Simpson, Hillsborough, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 56 days.

(21) Appl. No.: 10/363,603

(22) PCT Filed: Sep. 6, 2001

(86) PCT No.: PCT/US01/27644

§ 371 (c)(1),
(2), (4) Date: Jul. 7, 2003

(87) PCT Pub. No.: WO02/20721

PCT Pub. Date: Mar. 14, 2002

(65) Prior Publication Data

US 2004/0030117 A1 Feb. 12, 2004

Related U.S. Application Data

(60) Provisional application No. 60/230,663, filed on Sep. 7, 2000.

(51) Int. Cl.
*A61K 39/12* (2006.01)
*C12N 7/01* (2006.01)
*C12N 15/40* (2006.01)
*C12N 15/86* (2006.01)

(52) U.S. Cl. ............... 424/199.1; 424/93.2; 536/23.72; 435/235.1; 435/236; 435/320.1; 435/325; 435/471; 435/472

(58) Field of Classification Search .............. 536/23.72; 435/235.1, 236, 325, 471, 472, 320.1; 424/199.1, 424/93.2
See application file for complete search history.

(56) References Cited

U.S. PATENT DOCUMENTS

| 4,650,764 A | 3/1987 | Temin et al. |
| 5,091,309 A | 2/1992 | Schlesinger et al. |
| 5,185,440 A | 2/1993 | Davis et al. |
| 5,217,879 A | 6/1993 | Huang et al. |
| 5,505,947 A | 4/1996 | Johnston et al. |
| 5,639,650 A | 6/1997 | Johnston et al. ............ 435/236 |
| 5,643,576 A | 7/1997 | Johnston et al. |
| 5,739,026 A | 4/1998 | Garoff et al. ............ 435/320.1 |
| 5,766,602 A | 6/1998 | Xiong et al. ............. 424/218.1 |
| 5,789,245 A | 8/1998 | Dubensky et al. ........ 435/320.1 |
| 5,792,462 A | 8/1998 | Johnston et al. ......... 424/199.1 |
| 5,811,407 A | 9/1998 | Johnston et al. ............... 514/44 |
| 5,814,482 A | 9/1998 | Dubensky, Jr. et al. .... 435/69.3 |
| 5,843,723 A | 12/1998 | Dubensky, Jr. et al. .... 435/69.3 |
| 6,008,035 A | 12/1999 | Johnston et al. ......... 435/235.1 |
| 6,015,694 A | 1/2000 | Dubensky et al. .......... 435/69.3 |
| 6,156,304 A | 12/2000 | Glorioso et al. ............ 424/93.2 |
| 6,156,558 A | 12/2000 | Johnston et al. .......... 435/235.1 |
| 6,190,666 B1 | 2/2001 | Garoff et al. ............. 424/208.1 |
| 6,224,879 B1 | 5/2001 | Sjöberg et al. ........... 424/218.1 |
| 6,242,259 B1 | 6/2001 | Polo et al. .................. 435/456 |
| 6,521,235 B2 | 2/2003 | Johnston et al. ......... 424/199.1 |
| 6,531,135 B1 | 3/2003 | Johnston et al. ......... 424/199.1 |
| 6,541,010 B1 | 4/2003 | Johnston et al. ......... 424/199.1 |
| 6,583,121 B1 | 6/2003 | Johnston et al. .............. 514/44 |
| 2001/0016199 A1 | 8/2001 | Johnston et al. ......... 424/199.1 |

FOREIGN PATENT DOCUMENTS

| WO | WO92/10578 | 6/1992 |
| WO | WO/95/07994 | 3/1995 |
| WO | WO95/27044 | 10/1995 |
| WO | WO95/31565 | 11/1995 |
| WO | WO96/17072 | 6/1996 |
| WO | WO96/37220 | 11/1996 |
| WO | WO96/37616 | 11/1996 |
| WO | WO97/38087 | 10/1997 |
| WO | 98/36779 | * 8/1998 |
| WO | WO99/51263 | 10/1999 |
| WO | WO00/39318 | 7/2000 |
| WO | WO01/16343 | 3/2001 |

OTHER PUBLICATIONS

Li et al PNAS 93:11658–11663, 1996.*

Frolov et al., "Translation of Sindbis Virus mRNA: Analysis of Sequences Downstream of the Initiationg AUG Codon That Enhance Translation," *Journal of Virology* 70(2): 1182–1190 (1996).

International Search Report for the corresponding International Application No. PCT/US01/27644.

"Sindbis Virus (HRSP and Wild–Type Strains), Complete Genome," *EMBL Database, Accession Nos. J02363, 02364, J02366, J02367, and V00073*, (Jul. 3, 1991).

Bredenbeek et al, *Sindbis Virus Expression Vectors: Packaging of RNA Replicons by Using Defective Helper RNAs, Journal of Virology* 67 No. 11, pp. 6439–6446 (1993).

(Continued)

Primary Examiner—Mary E. Mosher
(74) Attorney, Agent, or Firm—Myers Bigel Sibley & Sajovec, P.A.

(57) ABSTRACT

Provided herein are alphavirus vectors derived from South African Arbovirus No. 86 (S.A.AR86) comprising attenuating mutations and methods of making the same. Also provided are improved viral vectors and helper constructs comprising a S.A.AR86 capsid enhancer sequence. The present invention also provides S.A.AR86 replicon and helper constructs comprising an alphavirus capsid enhancer sequence. Further provided are methods of administering an alphavirus vector comprising a heterologous nucleotide sequence (preferably encoding an immunogen or a therapeutic polypeptide) according to the invention to a cell or subject. In preferred embodiments, the alphavirus vector delivers the heterologous nucleotide sequence to the cells of the bone, bone marrow, and/or bone-associated connective tissue.

48 Claims, 8 Drawing Sheets

OTHER PUBLICATIONS

Bulychyov et al., "Disease Course in Guinea Pigs After Aerogenous Infection with Venezuelan Equine Encaphalomyelits Virs," (1995).

Corsini et al.: *Efficiency of Transduction by Recombinant Sindbis Replicon Virus Varies Among Cell Lines, Including Mosquito Cells and Rat Sensory Neurons,* BioTechniques, 21:3 (492–497), Sep. 1996.

Davis et al, *A Genetically Engineered Live Virus Vaccine for Venezuelan Equine Encephalitis;* J Cell Biochemistry Supplement O No. 17 Part D, issued 1993, Abstract N404.

Davis et al, *Attenuated Mutants of Venezuelan Equine Encephalitis Virus Containing Lethal Mutations in the PE2 Cleavage Signal Combined with a Second–Site Suppressor Mutation in E1,* Virology 212:102–110 (1995).

Davis et al., *Attenuating Mutations in the E2 Glycoprotein Gene of Venezuelan Equine Encephalitis Virus: Construction of Single and Multiple Mutants in a Full–Length cDNA Clone,* Virology 183 20–31 (1991).

Davis, N.L., "A molecular genetic approach to the study of Venezuelan equine encephalitis virus pathogenesis." *Archives of Virology.* (1994), 99–109.

Dubensky, Jr. et al. "Sindbis Virus DNA–Based Expression Vectors: Utility for in Vitro and in Vivo Gene Transfer," *Journal of Virology,* 70:1 508–519 (Jan. 1996).

Frolov et al., "Translation of Sindbis Virus mRNA: Analysis of Sequences Downstream of the Initiating AUG Codon that Enhances Translation," *Journal of Virology,* 70:2 1182–1190 (Feb. 1996).

Frolov et al., *Alphavirus–based expression vectors: Stategies and applications,* Proc. Natl. Acad. Sci. USA, vol. 93, pp. 11371–11377 (1996).

Frolov et al., "Translation of Sindbis Virus in RNA: Effects of Sequences Downstream of the Initiating Codon," *Journal of Virology,* 68 8111–end (1994).

Frolova et al., "Packaging Signals in Alphaviruses," *Journal of Virology,* 71 248–258 (Jan. 1997).

Geigenmuller–Gnirke et al. "Complementation Between Sindbis Viral RNAs Produces Infectious Particles with a Bipartite Genome." *Proceedings of the National Academy of Sciences of the United States of America,* vol. 88, Issue 8 (Apr. 15, 1991), 3253–3257.

Grieder et al., *Specific Restrictions in the Progression of Venezuelan Equine Encephalitis Virus–Induced Disease Resulting from Single AminoAcid Changes in the Glycoproteins,* Virology, 206, pp. 994–1006 (1995).

Hahn et al., "Infectious Sindbis Virus Transient Expression Vectors for Studying Antigen Processing and Presentation," *Proc. Natl. Acad. Sci. USA,* 89 2679–2683 (1992).

Heise et al., "A Single Amino Acid Change in nsP1 Attenuates Neuroviolence of the Sindbis–Group Alphavirus S.S.AR86," *Journal of Virology,* 74:9 (May 2000), 4207–4213.

Heise et al., "Adult Mouse Neurovirulence Determinants Within the Nonstructural Genes of the Sindbis–Group Alphavirus S.A.AR86," *American Society of Virology Meeting, Colorado,* Oral Presentation (Jul. 11, 2000).

Heise et al., "Sindbis–Group Alphavirus Replication in Periosteum and Endosteum of Long Bones in Adult Mice," *Journal of Virology,* 74:19 9294–9299 (Oct. 2000—published on–line Sep. 11, 2000).

Heise et al., "The Role of Viral Nonstructural Genes in Neuroviruience of the Sindbis–Group Virus, S.A.AR86," *Keystone Symposia, Taos, New Mexico,* 306 (Feb. 2000).

Hodgson et al., "Expression of Venezuelan Equine Encephalitis Virus Proteins by Recombinant Baculoviruses," *The American Journal of Tropical Medicine and* Hygiene, 49:3. 195–196 (1993).

Kinney, Richard, "Attenuation of Venzuelan Equine Ecephalitis Virus Strain TC–83 Is Encoded by the 5'–Noncoding Region and the E2 Envelope Glycoprotein." *Journal of Virology.* vol. 67, No. 3, (Mar. 1993), 1269–1277.

Lemm et al., *Polypeptide requirements for assembly of functional Sindbis virus replication complexes: a model for the temporal regulation of minus– and plus–strand RNA synthesis,* The EmBO Journal, vol. 13, No. 12, pp. 2925–2934 (1994).

Liljeström et al., *A New Generation of Animal Cell Expression Vectors Based on the Semliki Forest Virus Replicon,* Bio/Technology, vol. 9, Dec. 1991, pp. 1356–1361.

Liljeström, Peter, "Alphavirus expression systems." *Current Opinion in Biotechnology.* vol. 5, No. 5, (Oct. 1994), 495–500.

Liljeström, Peter, "Alphavirus Vectors for Gene Delivery," *OECD Documents, Gene Delivery Systems,* 109–118 (1996).

London et al., "Infectious Enveloped RNA Virus Antigenic Chimeras," *Proc. Natl. Acad. Sci. USA,* 89 207–211 (1992).

Lvov et al., "'Karshi' Virus, a New Flavivirus (Togaviridae) Isolated from Ornithodoros Papillipes (Birula, 1895) Ticks in Uzbek S.S.R.," *Archives of Virology,* 50 29–36 (1976).

McKnight et al., "Deduced Consensus Sequences of Sindbis Virus Strain AR339: Mutations Contained in Laboratory Strains which Affect Cell Culture and in Vivo Phenotypes," *Journal o f Virology,* 70(3) 1981–1989 (1996).

Morgenstein et al, *Advanced mammalian gene transfer: high titre retroviral vectors with multiple drug selection markers and a complementary helper–free packaging cell line,* Nucleic Acids Research 18:No. 12, pp. 3587–3596 (1990).

Orkin et al., "Report and Recommendation of the Panel to Assess the NIH Investment in Research on Gene Therapy," 1–41 (1995).

Polo et al., *Attenuating Mutations in Glycoproteins E1 and E2 of Sindbis Virus Produce a Highly Attenuated Strain When Combined in Vitro,* Journal of Virology 64 No. 9, pp. 4438–4444 (1990).

Russell et al., *Sindbis Virus Mutations Which Coordinately Affect Glycoprotein Processing, Penetration, and Virulence in Mice,* Journal of Virology, vol. 63, No. 4, Apr. 1989, pp. 1619–1629.

Schlesinger et al., "Recombination between Sindbis virus RNAs." *Archives of Virology,* Suppl. 9, (1994), 213–220.

Schlesinger, Sondra, "Alphaviruses—vectors for the expression of heterologous genes." *TiBTech.* (1993), 18–22.

Schoepp et al., *Directed Mutagenesis of a Sindbis Virus Pathogenesis Site;* Virology 193, pp. 149–159 (1993).

Simpson et al., "Sindbis–Like Virus Isolate Girdwood S.A., Complete Genome," *EMBL Database, Accession No. U38304,* (Jan. 3, 1996).

Simpson et al., *Complete Nucleotide Sequence and Full–Length cDNA Clone of S.A.AR86, a South African Alphavirus Related to Sindbis[1],* Virology 222 (464–469) Article No. 0445, 1996.

Sjöberg et al., "A Significantly Improved Semliki Forest Virus Expression System Based on Translation Enhancer Segments from the Viral Capsid Gene." *Bio/Technology.* vol. 12, (Nov. 1994), 1127–1131.

Smerdou et al., "Two–Helper RNA System for Production of Recombinant Semliki Forest Virus Particles," *Journal of Virology*, 73:2 1092–1098 (Feb. 1999).

Strauss et al., *The Alphaviruses: Gene Expression, Replication, and Evolution, Microbiological Reviews*, Sep. 1994, pp. 491–562.

Suomalainen et al., *Spike Protein–Nucleocapsid Interactions Drive the Budding of Alphaviruses, J. Virology*, vol. 66, No. 8, pp. 4737–4747 (1992).

Tuittila et al., "Replicase Complex Genes of Semliki Forest Virus Confer Lethal Neurovirulence," *Journal of Virology*, 74:10 4579–4589 (May 2000).

Weiss et al., "Recombination between Sindbis Virus RNAs." *Journal of Virology*. vol. 65, No. 8 (Aug. 1991), 4017–4025.

Xiong et al., "Sindbis Virus: An Efficient, Broad Host Range Vector for Gene Expression in Animal Cells." *Science,* New Series, vol. 243, Issue 4895 (Mar. 3, 1989), 1188–1191.

* cited by examiner

SEQUENCE LISTING

<160> NUMBER OF SEQ ID NOS: 1

<210> SEQ ID NO 1
<211> LENGTH: 18
<212> TYPE: PRT
<213> ORGANISM: Artificial sequence
<220> FEATURE:
<223> OTHER INFORMATION: Synthetic peptide

<400> SEQUENCE: 1

Ile Thr Ser Met Asp Ser Trp Ser Ser Gly Pro Ser Ser Leu Glu Ile
1               5                   10                  15

Val Asp

VECTORS DERIVED FROM SOUTH AFRICAN ARBOVIRUS NO. 86

RELATED APPLICATION INFORMATION

This application claims priority under 35 U.S.C. §371 from PCT Application No. PCT/US01/27644, filed on Sep. 6, 2001, which claims the benefit of U.S. provisional Application Ser. No. 60/230,663, filed on Sep. 7, 2000; the disclosures of which applications are incorporated by reference herein in their entireties.

STATEMENT OF FEDERAL SUPPORT

The present invention was made with government support under grant numbers RO1 AI22186, RO1 AR47190, postdoctoral institutional training grant T 32 AI07151, and postdoctoral fellowship F32 AI10146 from the National Institute of Health. The United States government has certain rights to this invention.

FIELD OF THE INVENTION

The present invention relates to alphavirus vectors and methods of making and administering the same, in particular, the present invention relates to alphavirus vectors derived from South African Arbovirus No. 86, and methods of making an administering the same.

BACKGROUND OF THE INVENTION

Several old world alphaviruses, including the Sindbis-group viruses, Ross River virus, O'nyong-nyong and Chikungunya, are associated with outbreaks of acute and persistent arthritis/arthralgia in humans (reviewed in Johnston, R. E. and C. J. Peters. 1996. Alphaviruses, p. 843–898. In B. N. Fields, D. M. Knipe, and P. M. Howley (eds.), Fields Virology. Lippincott-Raven, Philadelphia). Chikungunya and O'nyong-nyong have caused massive epidemics of acute, debilitating arthralgia in Africa and Asia (Id.). Ross River virus, also known as epidemic polyarthritis, is endemic to Australia (Aaskov et al., (1985) *Aust. J. Exp. Biol. Med. Sci.* 5:587; Johnston, R. E. and C. J. Peters. 1996. Alphaviruses, p. 843–898. In B. N. Fields, D. M. Knipe, and P. M. Howley (eds.), Fields Virology. Lippincott-Raven, Philadelphia; Tai et al., (1993) *Med. J. Aust.* 158:522), and caused a major epidemic that swept the South Pacific Islands in 1979, affecting 50,000 people on the Island of Fiji (Aaskov et al., (1981) *Am. J. Trop. Med. Hyg.* 30:1053). Sindbis-group alphaviruses, including Ockelbo, Karelian fever virus, and GirdwoodS.A. are associated with acute and persistent arthralgia in Northern Europe and South Africa (Malherbe et al., (1963) *S. Afr. Med. J.* 37:547; Skogh et al., (1982) *Lancet* i:795; Tesh et al., (1982) *Ann. Rev. Med.* 33:31). Ockelbo disease; one of the best characterized of the Sindbis-group alphavirus arthralgias, is often incapacitating (Johnston, R. E. and C. J. Peters. 1996. Alphaviruses, p. 843–898. In B. N. Fields, D. M. Knipe, and P. M. Howley (eds.), Fields Virology. Lippincott-Raven, Philadelphia; Tesh et al., (1982) *Ann. Rev. Med.* 33:31), and one study found that symptoms lasted for months to years in 31% of patients (Niklasson et al., (1986) *Lancet* 1:1039). Symptoms include arthralgia in one or more joints, including large joints such as the knee, hip, and elbow (reviewed in Johnston, R. E. and C. J. Peters. 1996. Alphaviruses, p. 843–898. In B. N. Fields, D. M. Knipe, and P. M. Howley (eds.), Fields Virology. Lippincott-Raven, Philadelphia; Tesh et al., (1982) *Ann. Rev. Med.* 33:31). Pain within or around tendons is also a common trait of Sindbis-group virus infections (Tesh et al., (1982) *Ann. Rev. Med.* 33:31). Rubella virus, another member of the family Togaviridae that is distantly related to the alphaviruses, is also associated with acute and persistent arthritis in humans (reviewed in Wolinsky, J. S. 1996. Rubella, p. 899–929. In B. N. Fields, D. M. Knipe, and P. M. Howley (eds.), Field's Virology. Lippencott-Raven, Philadelphia).

Mechanisms underlying Togavirus induced arthralgia/arthritis are not clearly understood, though direct viral replication within or around the affected joints may contribute to disease (reviewed in Tesh et al., (1982) *Ann. Rev. Med.* 33:31). Ross River virus antigen has been detected in cell aspirates from the joints of acutely infected individuals (Fraser et al., (1983) *J. Clin. Path.* 36:1256). Furthermore, patients suffering from persistent arthralgia following Ockelbo virus infection often have high levels of Ockelbo virus specific IgM, which suggests that the virus may persistently infect these individuals (Niklasson et al., (1988) *J. Infect. Dis.* 157:832).

Understanding of the mechanisms leading to alphavirus mediated arthritis/arthralgia in humans has been hampered by the lack of a small animal model. Sindbis-group alphaviruses, Semliki Forrest virus, and Ross River virus replicate in bone associated connective tissue in neonatal mice, however skin and muscle are also major sites of viral replication (Klimstra et al., (1999) *J. Virol.* 73:10387; Murphy et al., (1970) *Lab. Invest.* 22:318; Murphy et al., (1973) *Journal of Infectious Disease* 127:129; Trgovcich et al., (1996) *Virol.* 224:73). Furthermore, infection of neonatal animals with these viruses results in rapidly fatal disease (Id.). This generalized pattern of replication and lethal outcome in neonatal mice has limited their usefulness as a model of bone and/or joint replication by arthralgia associated alphaviruses.

The present invention addresses a need in the art for improved alphavirus vectors and methods of administering the same.

SUMMARY OF THE INVENTION

The present invention is based, in part, on the discovery of improved reagents derived from South African Arbovirus No. 86 (S.A.AR86). Based on sequence comparisons, S.A.AR86 is in a subgroup of the Sindbis-group viruses that also includes GirdwoodS.A. and Ockelbo. Of these viruses, only S.A.AR86 is neurovirulent in weanling and adult mice, causing 90% to 100% mortality in mice of any age. The complete genomic sequence of S.A.AR86 is available (see Simpson et al., (1996) *Virology* 222:464; U.S. Pat. Nos. 5,639,650; 5,811,407; GenBank accession number 146902; the disclosures of which are incorporated herein by reference in their entireties).

It has previously been reported that alphavirus vectors, including S.A.AR86 vectors, infect and exhibit long-term persistence in the cells of the bone marrow (e.g. osteoblasts), in particular, the cells of the endosteum, more particularly, endosteum cells within synovial joints. As one aspect, the present investigations have further characterized the targeting, expression and persistence of vectors derived from S.A.AR86.

S.A.AR86 infects bone cells, as well as cells of the bone marrow and bone-associated connective tissue. In particular, S.A.AR86 infects the cells of the periosteum, endosteum and tendons, generally within the epiphyses of the long bones adjacent to joints. Osteoblasts, among other cells, are targeted by S.A.AR86 in the periosteum and endosteum, whereas the target cells in tendons appear to be fibroblasts.

Cells that may be infected by the alphavirus vectors of the present invention include, but are not limited to, polymorphonuclear cells, hemopoietic stem cells (including megakaryocyte colony forming units (CFU-M), spleen colony forming units (CFU-S), erythroid colony forming units (CFU-E), erythroid burst forming units (BFU-E), and colony forming units in culture (CFU-C)), erythrocytes, macrophages (including reticular cells), monocytes, granulocytes, megakaryoctyes, lymphocytes, fibroblasts, osteoprogenitor cells, osteoblasts, osteoclasts, marrow stromal cells, chondrocytes and other cells of synovial joints.

The persistence of S.A.AR86 vectors, and other alphavirus vectors as disclosed herein and U.S. Pat. No. 5,811,407, in the cells of the bone, bone marrow, and bone-associated connective tissue may advantageously be employed in methods of producing an immune response and/or for methods of therapeutic gene delivery to the cells of the bone and bone marrow, as well as bone-associated connective tissue and neurons. Preferably, the alphavirus vector persists at detectable levels within the cell for at least about one month, at least about two months, at least about three months, at least about four months, at least about six months, at least about nine months, at least about twelve months, or longer. More preferably, persistence at detectable levels is for a period of at least about three months.

As a further aspect, the present invention provides a S.A.AR86 genomic RNA, said S.A.AR86 genomic RNA comprising: (a) S.A.AR86 nonstructural protein (nsp) coding sequences, wherein the S.A.AR86 nonstructural protein coding sequences encode an attenuating mutation selected from the group consisting of:

(i) an attenuating mutation in the cleavage domain between the nsp1 and nsp2 coding sequences;

(ii) an attenuating mutation that results in a termination codon at nsp3 amino acid position 537, (iii) an attenuating mutation comprising a substitution mutation at nsP3 amino acid position 385, (iv) an attenuating mutation comprising an insertion of at least 8 amino acids following nsP3 amino acid position 385, (v) a combination of the attenuating mutations of (i) to (iv), and (b) a heterologous nucleotide sequence. In particular embodiments, the genomic RNA further comprises an alphavirus capsid enhancer sequence operatively associated with the heterologous nucleotide sequence.

As another aspect, the present invention provides a S.A.AR86 genomic RNA comprising (a) an alphavirus capsid enhancer sequence, and (b) a heterologous nucleotide sequence. In embodiments of the invention, the alphavirus capsid enhancer sequence is operably associated with the heterologous nucleotide sequence, so that expression of the heterologous nucleotide sequence is enhanced as compared to the level of expression in the absence of the capsid enhancer sequence.

As a further aspect, the present invention provides an infectious alphavirus particle comprising: (a) assembled alphavirus structural proteins, and (b) a S.A.AR86 genomic RNA according to the invention packaged within the assembled alphavirus structural proteins.

Also provided a compositions and pharmaceutical formulations comprising a plurality of the alphavirus particles of the invention.

As a still further aspect, the present invention provides a method of introducing a nucleotide sequence into a cell, comprising contacting a cell in vitro with an alphavirus particle according to the invention under conditions wherein the heterologous nucleotide sequence is introduced into the cell. The cell may be administered to a subject, e.g., in ex vivo methods of gene transfer, or an antigen presenting cell (such as a dendritic cell) may be administered to the subject to provide immunity.

As a yet further aspect, the present invention provides a method of administering a nucleotide sequence to a subject, comprising administering to the subject an alphavirus particle according to the present invention in a pharmaceutically acceptable carrier. In particular embodiments, the nucleotide sequence is administered in a method of producing an immune response.

The present invention also provides helper cells and methods for producing replicon particles according to the present invention.

As a further aspect, the present invention provides, a DNA molecule comprising: (a) a segment encoding a S.A.AR86 genomic RNA according to the invention, and (b) a promoter operatively associated with the segment encoding the S.A.AR86 genomic RNA. Also provided are infectious RNA transcripts encoded by the DNA molecule, vectors comprising the DNA vector, and cells comprising the vector.

These and other aspects of the invention are described in more detail in the description of the invention set forth below.

DETAILED DESCRIPTION OF THE INVENTION

Figure 1:
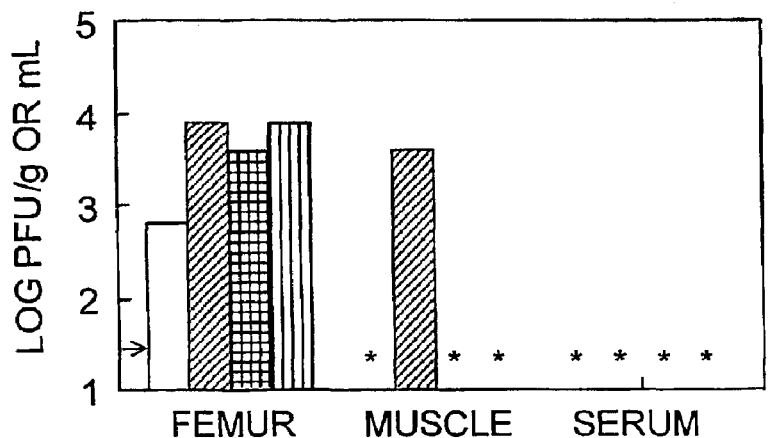
FIG. 1. S.A.AR86, as well as other Sindbis-group alphaviruses, replicates in bone/joint associated tissues. A. Six week old female CD-1 mice were infected with $10^3$ pfu of s55 i.v. Three days post infection, mice were sacrificed, exsanguinated, perfused with PBS, and femurs and quadriceps muscles removed by dissection and titered for infectious virus on BHK-21 cells. Data is shown as Log pfu/gram of tissue for femur and muscle, and as pfu/ml for serum. Each bar represents a single animal. The arrow indicates the limit of detection and asterisks denote samples below the limit of detection. Data shown is from one of four experiments. B. Six week old female CD-1 mice were infected i.v. with $10^3$ pfu of s51, sacrificed three days post-infection, and the right femur was removed for virus titration. Bone marrow was aspirated from the diaphysis of the femur using 0.4 ml PBS/1% DCS per femur. Aspirates were freeze/thawed and titrated for infectious virus by plaque assay. Following marrow aspiration, the remaining femoral tissue was processed as in 1A and titrated for infectious virus by plaque assay. Titer is shown as total pfu per marrow aspirate or femur (without aspirated marrow) with each bar representing a single animal. The arrow indicates the limit of detection and asterisks denote samples with titers below the limit of detection. Shown is one of three comparable experiments. C. Six week old female CD-1 mice were infected iv with $10^3$ pfu of the viruses s55, TR339, or TRSB. Three days post infection mice were sacrificed, and both femurs removed for virus titration. Femurs were processed and titrated for infectious virus as in 1A. n=3 mice/group. The arrow indicates the limit of detection. N/D=not done. Shown is one of two comparable experiments.
Figure 1:
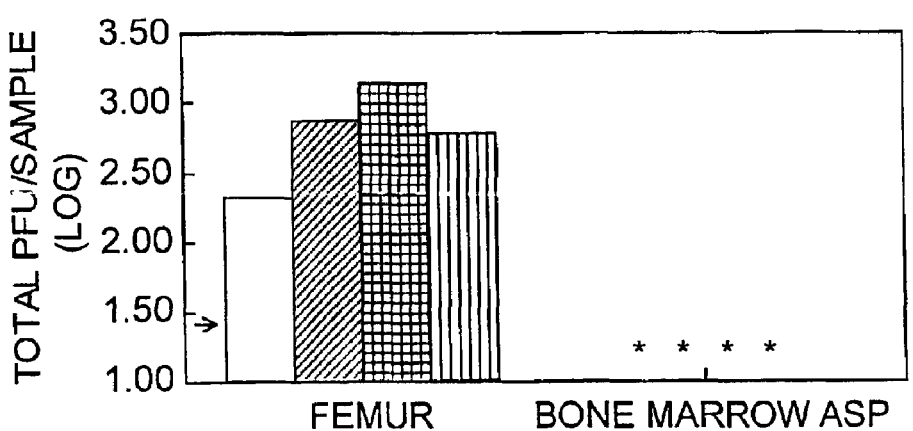
Figure 1:
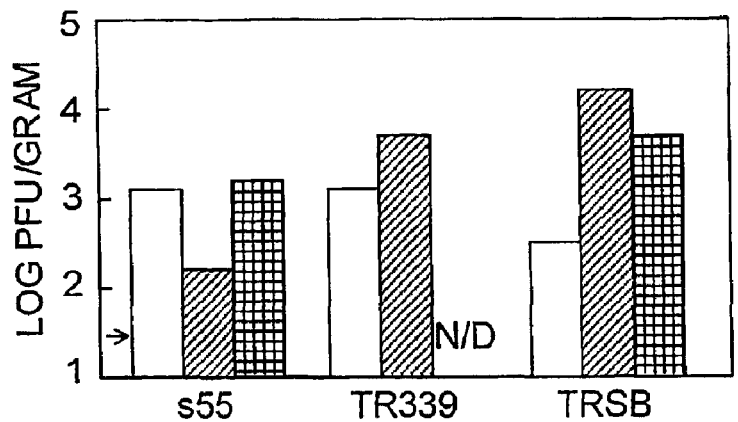

Except as otherwise indicated, standard methods known to those skilled in the art may be used for the construction and use of recombinant nucleotide sequences, vectors, helper constructs, transformed host cells, selectable markers, alphavirus vectors, viral infection of cells, production of attenuated viruses, and the like. Such techniques are known to those skilled in the art. See, e.g., SAMBROOK et al., MOLECULAR CLONING: A LABORATORY MANUAL 2nd Ed. (Cold Spring Harbor, N.Y., 1989); F. M. AUSUBEL et al. CURRENT PROTOCOLS IN MOLECULAR BIOLOGY (Green Publishing Associates, Inc. and John Wiley & Sons, Inc., New York).

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

As used herein, the term "polypeptide" encompasses both peptides and proteins.

The term "alphavirus" has its conventional meaning in the art, and includes Eastern Equine Encephalitis virus (EEE), Venezuelan Equine Encephalitis virus (VEE), Everglades virus, Mucambo virus, Pixuna virus, Western Encephalitis virus (WEE), Sindbis virus, South African Arbovirus No. 86 (S.A.AR86), Girdwood S.A. virus, Ockelbo virus, Semliki Forest virus, Middelburg virus, Chikungunya virus, O'Nyong-Nyong virus, Ross River virus, Barmah Forest virus, Getah virus, Sagiyama virus, Bebaru virus, Mayaro virus, Una virus, Aura virus, Whataroa virus, Babanki virus, Kyzlagach virus, Highlands J virus, Fort Morgan virus, Ndumu virus, Buggy Creek virus, and any other virus classified by the International Committee on Taxonomy of Viruses (ICTV) as an alphavirus.

Preferred alphaviruses for use in the present invention are Sindbis virus strains (e.g., TR339), S.A.AR86 virus, Girdwood S.A. virus, and Ockelbo virus, still more preferably, S.A.AR86, and chimeric viruses thereof.

An "Old World alphavirus" is a virus that is primarily distributed throughout the Old World. Alternately stated, an Old World alphavirus is a virus that is primarily distributed throughout Africa, Asia, Australia and New Zealand, or Europe. Exemplary Old World viruses include SF group alphaviruses and SIN group alphaviruses. SF group alphaviruses include Semliki Forest virus, Middelburg virus, Chikungunya virus, O'Nyong-Nyong virus, Ross River virus, Barmah Forest virus, Getah virus, Sagiyama virus, Bebaru virus, Mayaro virus, and Una virus. SIN group alphaviruses include Sindbis virus, South African Arbovirus No. 86, Ockelbo virus, Girdwood S.A. virus, Aura virus, Whataroa virus, Babanki virus, and Kyzylagach virus.

The phrase "alphavirus structural protein(s)" as used herein refers to one or more of the proteins that are required to produce a functional alphavirus particle that encapsidates the alphavirus genomic RNA. The alphavirus structural proteins include the capsid protein, E1 glycoprotein, E2 glycoprotein, E3 protein and 6K protein. The alphavirus particle comprises the alphavirus structural proteins assembled to form an enveloped nucleocapsid structure. As known in the art, alphavirus structural subunits consisting of a single viral protein, capsid, associate with themselves and with the RNA genome to form the icosahedral nucleocapsid, which is then surrounded by a lipid envelope covered with a regular array of transmembranal protein spikes, each of which consists of a heterodimeric complex of two glycoproteins, E1 and E2 (See Paredes et al., (1993) *Proc. Natl. Acad. Sci. USA* 90, 9095–99; Paredes et al., (1993) *Virology* 187, 324–32; Pedersen et al., (1974) *J. Virol.* 14:40).

An alphavirus "genomic RNA" indicates the alphavirus RNA transcript. The wild-type alphavirus genome is a single-stranded, messenger-sense RNA, modified at the 5'-end with a methylated cap, and at the 3'-end with a variable-length poly (A) tract. The viral genome is divided into two regions: the first encodes the nonstructural or replicase proteins (nsP1-nsP4) and the second encodes the viral structural proteins (Strauss and Strauss, *Microbiological Rev.* (1994) 58:491–562). As used herein, the term "genomic RNA" encompasses recombinant alphavirus genomes (e.g., containing a heterologous nucleotide sequence), viral genomes containing one or more attenuating mutations, deletions, insertions, and/or otherwise modified viral genomes. For example, the "genomic RNA" may be modified to form a double-promoter molecule or a replicon (each as described below).

A "chimeric" alphavirus as used herein comprises the alphavirus structural proteins and a genomic RNA from another alphavirus. In embodiments of the invention, the chimeric alphavirus comprises a S.A.AR86 genomic RNA and alphavirus structural proteins from another alphavirus (e.g., Sindbis, GirdwoodS.A., Ockelbo, and the like). In other embodiments of the invention, the chimeric alphavirus comprises S.A.AR86 alphavirus structural proteins and a genomic RNA from another alphavirus (e.g., Sindbis, GirdwoodS.A., Ockelbo, and the like). In particular embodiments, the alphavirus structural proteins comprise structural proteins from two or more alphaviruses.

An "infectious" alphavirus particle is one that can introduce the alphavirus genomic RNA into a permissive cell, typically by viral transduction. Upon introduction into the target cell, the genomic RNA serves as a template for RNA transcription (i.e., gene expression). The "infectious" alphavirus particle may be "replication-competent" (i.e., can transcribe and replicate the alphavirus genomic RNA) and "propagation-competent" (i.e., results in a productive infection in which new alphavirus particles are produced). In embodiments of the invention, the "infectious" alphavirus particle is a replicon particle (as described below) that may introduce the genomic RNA (i.e., replicon) into a host cell, is "replication-competent" to replicate the genomic RNA, but is "propagation-defective" in that it is unable to produce new alphavirus particles in the absence of helper sequences that complement the deletions or other mutations in the replicon (i.e., provide the structural proteins that are not provided by the replicon).

As used herein, an "isolated" nucleic acid (e.g., an "isolated DNA" or an "isolated genomic RNA") means a nucleic acid separated or substantially free from at least some of the other components of the naturally occurring organism or virus, for example, the cell or viral structural components or other polypeptides or nucleic acids commonly found associated with the nucleic acid.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

As used herein, the terms "deleted" or "deletion" mean either total deletion of the specified segment or the deletion of a sufficient portion of the specified segment to render the segment inoperative or nonfunctional, in accordance with standard usage See, e.g., U.S. Pat. No. 4,650,764 to Temin et al.).

I. Alphavirus Vectors.

The present invention is practiced using alphavirus vectors, more preferably a propagation-incompetent alphavirus vector, still more preferably an alphavirus replicon vector (as described below). Alphavirus and replicon vectors are described in U.S. Pat. No. 5,505,947 to Johnston et al.; U.S. Pat. No. 5,792,462 to Johnston et al., U.S. Pat. No. 5,814,482 to Dubensky et al., U.S. Pat. No. 5,843,723 to Dubensky et al., U.S. Pat. No. 5,789,245 to Dubensky et al., U.S. Pat. No. 5,739,026 to Garoff et al., the disclosures of which are incorporated herein by reference in their entireties. More preferably, the alphavirus vector is a S.A.AR86 vector, a S.A.AR86 replicon vector, or S.A.AR86 chimeric vector comprising a S.A.AR86 genomic RNA.

Alphavirus vectors elicit a strong host response to immunogen. While not wishing to be held to any particular theory of the invention, it appears that alphavirus vectors induce a more balanced and comprehensive immune response (i.e., cellular and humoral immunity) than do conventional vaccination methods. Moreover, it appears that alphavirus vectors induce a strong immune response, in part, because they directly infect and replicate within dendritic cells. The resulting presentation of antigen to the immune system induces a strong immune response. The alphavirus 26S subgenomic promoter also appears to give high level of expression of a heterologous nucleic acid encoding antigen.

The alphavirus vector preparation may be partially or highly purified, or may be a relatively crude cell lysate or supernate from a cell culture, as known in the art.

The alphavirus vector may be a chimeric alphavirus, as that term is understood in the art. For example, the alphavirus structural proteins may be from one alphavirus (preferably, S.A.AR86) and the nucleic acid packaged within the capsid may be from another alphavirus. Alternatively, the alphavirus virus may be assembled from structural proteins derived from more than one alphavirus.

A. Double Promoter Vectors.

In one embodiment of the invention, the alphavirus genomic RNA is a double promoter. A double promoter vector is a replication and propagation competent virus. Double promoter vectors are described in U.S. Pat. Nos. 5,185,440, 5,505,947 and 5,639,650, the disclosures of which are incorporated in its entirety by reference. Preferred alphaviruses for constructing the double promoter vectors are S.A.AR86, Girdwood S.A., TR339 and Ockelbo viruses. Exemplary double promoters are derived from a S.A.AR86 genomic RNA. More preferably, the double promoter vector contains one or more attenuating mutations. Attenuating mutations are described in more detail hereinbelow.

In preferred embodiments, the double promoter vector is constructed so as to contain a second subgenomic promoter (i.e., 26S promoter) inserted 3' to the virus RNA encoding the structural proteins. The heterologous RNA is inserted between the second subgenomic promoter, so as to be operatively associated therewith, and the 3' UTR of the virus genome. Heterologous RNA sequences of less than 3 kilobases, more preferably those less than 2 kilobases, and more preferably still those less than 1 kilobase, can be inserted into the double promoter vector. In a preferred embodiment of the invention, the double promoter vector is derived from a Girdwood S.A. genomic RNA, and the second subgenomic promoter is a duplicate of the Girdwood S.A. subgenomic promoter. In an alternate preferred embodiment, the double promoter vector is derived from a Sindbis (e.g., TR339) genomic RNA, and the second subgenomic promoter is a duplicate of the TR339 subgenomic promoter. In another preferred embodiment, the double promoter vector is derived from a S.A.AR86 genomic RNA, and the second subgenomic promoter is a duplicate of the S.A.AR86 subgenomic promoter.

B. Replicon Vectors.

Replicon vectors, which are infectious, propagation-defective, virus vectors can also be used to carry out the present invention. Replicon vectors are described in more detail in WO 96137616 to Johnston et al., U.S. Pat. No. 5,505,947 to Johnston et al., and U.S. Pat. No. 5,792,462 to Johnston et al. Preferred alphaviruses for constructing the replicon vectors according to the present invention are S.A.AR86, Girdwood S.A., Sindbis (e.g., TR339), and Ockelbo, and chimeras thereof.

In general, in the replicon system, a foreign gene to be expressed is inserted in place of at least a portion of one or more of the viral structural protein genes in a transcription vector containing the viral sequences necessary for viral replication (e.g., the nsp1–4 genes). RNA transcribed from this vector contains sufficient viral sequences (e.g., the viral nonstructural genes) responsible for RNA replication and transcription. Thus, if the transcribed RNA is transfected into susceptible cells, it will be replicated and translated to give the replication proteins. These proteins will transcribe the transfected RNA, including the transgene, which will then be translated to produce high levels of the foreign protein. The autonomously replicating RNA (i.e., replicon) can only be packaged into virus particles if the deleted alphavirus structural protein genes are provided on one or more helper molecules, which are provided to the helper cell.

Preferably, the helper molecules do not contain the viral nonstructural genes for replication, but these functions are provided in trans by the replicon molecule. The transcriptase functions translated from the replicon molecule transcribe the structural protein genes on the helper molecule, resulting in the synthesis of viral structural proteins and packaging of the replicon into virus-like particles. As the alphavirus packaging or encapsidation signal is located within the nonstructural genes, the absence of these sequences in the helper molecules precludes their incorporation into virus particles.

Accordingly, the replicon molecule is "propagation defective," as described hereinabove. The resulting alphavirus particles are propagation defective inasmuch as the replicon RNA in these particles does not include all of the alphavirus structural proteins required for encapsidation, at least a portion of at least one of the required structural proteins being deleted therefrom, such that the replicon RNA initiates only an abortive infection; no new viral particles are produced, and there is no spread of the infection to other cells.

Typically, the replicon molecule comprises an alphavirus packaging signal.

The replicon molecule is self-replicating. Accordingly, the replicon molecule comprises sufficient coding sequences for the alphavirus nonstructural polyprotein so as to support self-replication. In embodiments of the invention, the replicon encodes the alphavirus nsP1, nsP2, nsP3 and nsP4 proteins.

The replicon molecules of the invention "do not encode" one or more of the alphavirus structural proteins. By "do(es) not encode" one or more structural proteins, it is intended that the replicon molecule does not encode a functional form of the one or more structural proteins and, thus, a complementing sequence must be provided by a helper or packaging cell to produce new virus particles. In embodiments of the invention, the replicon molecule does not encode any of the alphavirus structural proteins.

The replicon may not encode the structural protein(s) because the coding sequence is partially or entirely deleted from the replicon molecule. Alternatively, the coding sequence is otherwise mutated so that the replicon does not express the functional protein. In embodiments of the invention, the replicon lacks all or substantially all of the coding sequence of the structural protein(s) that is not encoded by the replicon, e.g., so as to minimize recombination events with the helper sequences.

In particular embodiments, the replicon molecule may encode at least one, but not all, of the alphavirus structural proteins. For example, the alphavirus capsid protein may be encoded by the replicon molecule. Alternatively, one or both of the alphavirus glycoproteins may be encoded by the replicon molecule. As a further alternative, the replicon may encode the capsid protein and either the E1 or E2 glycoprotein.

In more preferred embodiments, none of the alphavirus structural proteins are encoded by the replicon molecule. For example, all or substantially all of the sequences encoding the alphavirus capsid protein and glycoproteins may be deleted from the replicon molecule.

Preferably, a composition comprising a population of replicon particles of the invention contains no detectable-replication competent alphavirus particles. Replication-competent virus may be detected by any method known in the art, e.g., by neurovirulence following intracerebral injection into suckling mice, or by passage twice on alphavirus-permissive cells (e.g., BHK cells) and evaluation for virus induced cytopathic effects.

II. Attenuating Mutations.

The present invention also provides alphavirus genomic RNA and particles (e.g., S.A.AR86) including attenuating mutations. The phrases "attenuating mutation" and "attenuating amino acid," as used herein, mean a nucleotide sequence containing a mutation, or an amino acid encoded by a nucleotide sequence containing a mutation, which mutation results in a decreased probability of causing disease in its host (i.e., reduction in virulence), in accordance with standard terminology in the art. See, e.g., B. Davis et al., MICROBIOLOGY 132 (3d ed. 1980). The phrase "attenuating mutation" excludes mutations or combinations of mutations which would be lethal to the virus.

Appropriate attenuating mutations will be dependent upon the alphavirus used. Suitable attenuating mutations within the alphavirus genome will be known to those skilled in the art. Exemplary attenuating mutations include, but are not limited to, those described in U.S. Pat. No. 5,505,947 to Johnston et al., U.S. Pat. No. 5,185,440 to Johnston et al., U.S. Pat. No. 5,643,576 to Davis et al., U.S. Pat. No. 5,792,462 to Johnston et al., and U.S. Pat. No. 5,639,650 to Johnston et al., the disclosures of which are incorporated herein in their entirety by reference.

When the alphavirus structural proteins are from VEE, suitable attenuating mutations may be selected from the group consisting of codons at E2 amino acid position 76 which specify an attenuating amino acid, preferably lysine, arginine, or histidine as E2 amino acid 76; codons at E2 amino acid position 120 which specify an attenuating amino acid, preferably lysine as E2 amino acid 120; codons at E2 amino acid position 209 which specify an attenuating amino acid, preferably lysine, arginine or histidine as E2 amino acid 209; codons at E1 amino acid 272 which specify an attenuating amino acid, preferably threonine or serine as E1 amino acid 272; codons at E1 amino acid 81 which specify an attenuating amino acid, preferably isoleucine or leucine as E1 amino acid 81; codons at E1 amino acid 253 which specify an attenuating amino acid, preferably serine or threonine as E1 amino acid 253; or the deletion of E3 amino acids 56–69, or a combination of the deletion of E3 amino acids 5659 together with codons at E1 amino acid 253 which specify an attenuating mutation, as provided above.

Also preferred are alphavirus vectors in which there is an attenuating mutation in the capsid protease that reduces, preferably ablates, the autoprotease activity of the capsid and results, therefore, in non-viable virus. Capsid mutations that reduce or ablate the autoprotease activity of the alphavirus capsid are known in the art, see e.g., WO 96/37616 to Johnston et al., the disclosure of which is incorporated herein in its entirety. In particular embodiments, the alphavirus vector comprises a VEE capsid protein in which the capsid protease is ablated, e.g., by introducing an amino acid substitution at VEE capsid position 152, 174, or 226. Alternatively, one or more of the homologous positions in other alphaviruses may be altered to reduce capsid protease activity.

If the alphavirus vector comprises a Sindbis-group virus (e.g., Sindbis, S.A.AR86, GirdwoodSA, Ockelbo) capsid protein, the attenuating mutation may be a mutation at capsid amino acid position 215 (e.g., a Ser→Ala) that reduces capsid autoprotease activity (see, Hahn et al., (1990) J. Virology 64:3069).

In particular, preferred, embodiments, the "attenuating" mutation reduces (e.g., by at least 25%, 40%, 50%, 60%, 70%, 80%, 90%, 95% or more) the neurovirulence of the alphavirus vector (e.g., as determined by intracerebral injection in weanling or adult mice). In embodiments of the invention, the attenuated virus is an attenuated S.A.AR86 virus vector (or chimeric vector, e.g., comprising a S.A.AR86 genomic RNA) with reduced neurovirulence.

It is not necessary that the attenuating mutations of the invention eliminate all pathology or adverse effects associated with virus administration, as long as there is some improvement or benefit (e.g., increased safety and/or reduced morbidity and/or reduced mortality) as a result of the attenuating mutation.

In other embodiments of the invention, the attenuating mutation does not result in a significant reduction in transgene expression from the attenuating alphavirus genomic RNA, i.e., transgene expression is essentially the same as in non-attenuated viruses. Alternatively, transgene expression may even be enhanced in the attenuated virus as compared with the non-attenuated virus.

When the alphavirus structural and/or non-structural proteins are from S.A.AR86, exemplary attenuating mutations in the structural and non-structural proteins include, but are not limited to, codons at nsP1 amino acid position 538 which specify an attenuating amino acid, preferably isoleucine as nsP1 amino acid 538; codons at E2 amino acid position 304 which specify an attenuating amino acid, preferably threonine as E2 amino acid 304; codons at E2 amino acid position 314 which specify an attenuating amino acid, preferably lysine as E2 amino acid 314; codons at E2 amino acid 372 which specify an attenuating amino acid, preferably leucine, at E2 amino acid residue 372; codons at E2 amino acid position 376 which specify an attenuating amino acid, preferably alanine as E2 amino acid 376; in combination, codons at E2 amino acid residues 304, 314, 372 and 376 which specify attenuating amino acids, as described above; codons at nsP2 amino acid position 96 which specify an attenuating amino acid, preferably glycine as nsP2 amino acid 96; and codons at nsP2 amino acid position 372 which specify an attenuating amino acid, preferably valine as nsP2 amino acid 372; in combination, codons at nsP2 amino acid residues 96 and 372 which encode attenuating amino acids at nsP2 amino acid residues 96 and 372, as described above; codons at nsP2 amino acid residue 529 which specify an attenuating amino acid, preferably leucine, at nsP2 amino acid residue 529; codons at nsP2 amino acid residue 571 which specify an attenuating amino acid, preferably asparagine, at nsP2 amino acid residue 571; codons at nsP2 amino acid residue 682 which specify an attenuating amino acid, preferably arginine, at nsP2 amino acid residue 682; codons at nsP2 amino acid residue 804 which specify an attenuating amino acid, preferably arginine, at nsP2 amino acid residue 804; codons at nsp3 amino acid residue 22 which specify an attenuating amino acid, preferably arginine, at nsP3 amino acid residue 22; and in combination, codons at nsP2 amino acid residues 529, 571, 682 and 804 and at nsP3 amino acid residue 22 which specify attenuating amino acids, as described above.

In particular preferred embodiments, the attenuating mutation is an attenuating mutation in one or more of the cleavage domains between the alphavirus nonstructural (nsp) genes, e.g., the nsP1/nsP2 cleavage region, the nsP2/nsP3 cleavage region, and/or the nsP3/nsP4 cleavage region. In embodiments of the invention, the attenuated virus includes an attenuating mutation in the nsP1/nsP2 cleavage region. Preferably, the attenuated virus comprises a S.A.AR86 genomic RNA comprising the attenuating mutation(s) in the nsp cleavage domain(s).

The cleavage regions between the alphavirus nonstructural proteins are fairly well conserved and have been discussed in Strauss and Strauss, *Microbiological Rev.* 58, 491–562, 494 (1994); the disclosure of which is incorporated herein in its entirety. In general, the amino acids in the cleavage domains have been designated, in the amino to carboxy terminus direction, as P4-P3-P2-P1↓P1'-P2'-P3'-P4' (arrow indicates the site of protease cleavage). Preferably, the attenuating mutation is at the P3 position of the cleavage domain.

In other embodiments of the invention, the attenuating mutation is in the P4, P3, P1' or P2' positions of the nsP1/nsP2 cleavage domain, which positions are less highly conserved among the various alphaviruses and likely to better withstand alterations.

In other embodiments of the invention, the attenuating mutation is in the cleavage domain between the S.A.AR86 nonstructural proteins. Exemplary attenuating mutations include attenuating mutations in the nsP1/nsP2 cleavage domain at amino acids 534–547 of the S.A.AR86 nonstructural polyprotein P1234, attenuating mutations in the nsP1/nsP2 cleavage domain at amino acids 537–544 of the S.A.AR86 nonstructural polyprotein P1234, attenuating mutations in the nsP2/nsP3 cleavage domain at amino acids 1341–1354 of the S.A.AR86 nonstructural polyprotein P1234, attenuating mutations in the nsP2/nsP3 cleavage domain at amino acids 1344–1351 of the S.A.AR86 nonstructural polyprotein P1234, attenuating mutations in the nsP3/nsP4 cleavage domain at amino acids 1884–1897 of the S.A.AR86 nonstructural polyprotein P1234, and attenuating mutations in the nsP3/nsP4 cleavage domain at amino acids 1887–1894 of the S.A.AR86 nonstructural polyprotein P1234.

In embodiments of the invention, the attenuating mutation is in the cleavage domain between the nsP1 and nsP2 genes of S.A.AR86. An exemplary attenuating mutation is a mutation at S.A.AR86 nsP1 amino acid 538 (position P3), more preferably a substitution mutation at S.A.AR86 nsP1 amino acid 538, still more preferably a Thr→Ile substitution at S.A.AR86 nsP1 amino acid 538.

The present inventors have found that a Thr→Ile substitution at S.A.AR86 nsP1 amino acid 538 may be incorporated into alphavirus vectors comprising S.A.AR86 nonstructural proteins to advantageously increase transgene expression (at the RNA or protein level), e.g., by at least about 2-fold, 5-fold, 10-fold or more, in particular, at early time-points post-infection (e.g., from about 0.5 to about 6 hours post-infection). In embodiments of the invention, the transgene is operatively associated with the 26S subgenomic promoter.

While not wishing to be held to any particular theory of the invention, it appears that the Thr→Ile attenuating mutation at S.A.AR86 nsP1 amino acid 538 enhances (i.e., increases) the rate of cleavage, thereby eliciting an augmented type I interferon response by the host, which may account for the attenuation. This view is supported by the finding that co-administration of attenuated and non-attenuated S.A.AR vectors results in attenuation of the non-attenuated virus.

Accordingly, the present invention encompasses other attenuating mutations in the nsp cleavage regions that result in an enhanced rate of cleavage and/or an enhanced type 1 interferon response. Methods of determining the rate of cleavage of the nsp polyprotein and/or interferon response may be by any method known in the art, including the methods disclosed herein (see, e.g., the Examples).

Likewise, those skilled in the art may identify attenuating mutations other than those specifically disclosed herein using other methods known in the art, e.g., looking at neurovirulence in weanling or adult mice following intracerebral injection.

To identify other attenuating mutations other than those specifically disclosed herein, amino acid substitutions may be based on any characteristic known in the art, including the relative similarity or differences of the amino acid side-chain substituents, for example, their hydrophobicity, hydrophilicity, charge, size, and the like.

Amino acid substitutions other than those disclosed herein may be achieved by changing the codons of the genomic RNA sequence (or a DNA sequence), according to the following codon table:

TABLE 1

| Amino Acids | | | Codons | | | | |
|---|---|---|---|---|---|---|---|
| Alanine | Ala | A | GCA | GCC | GCG | GCU | |
| Cysteine | Cys | C | UGC | UGU | | | |
| Aspartic acid | Asp | D | GAC | GAU | | | |
| Glutamic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG CGU |
| Serine | Ser | S | AGC | ACU | UCA | UCC | UCG UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

In identifying other attenuating mutations, the hydropathic index of amino acids may be considered. The importance of the hydropathic amino acid index in conferring interactive biologic function on a protein is generally understood in the art (see, Kyte and Doolittle, (1982) *J. Mol. Biol.* 157:105; incorporated herein by reference in its entirety). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, Id.), these are:

isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

Accordingly, the hydropathic index of the amino acid (or amino acid sequence) may be considered when identifying additional attenuating mutations according to the present invention.

It is also understood in the art that the substitution of amino acids can be made on the basis of hydrophilicity. U.S. Pat. No. 4,554,101 (incorporated herein by reference in its entirety) states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (±3.0); aspartate (+3.0±1); glutamate (+3.0±1); seine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Thus, the hydrophilicity of the amino acid (or amino acid sequence) may be considered when identifying additional attenuating mutations according to the present invention.

Other illustrative attenuating mutations include an attenuating mutation at amino acid position 537 of the S.A.AR86 nsP3 protein, more preferably a substitution mutation at this position (as described above; see Table I), still more preferably a nonsense mutation that results in substitution of a termination codon. Translational termination (i.e., stop) codons are known in the art, and include the "opal" (UGA), "amber" (UAG) and "ochre" (UAA) termination codons. In embodiments of the invention, the attenuating mutation results in a Cys→opal substitution at S.A.AR85 nsP3 amino acid position 537.

Further exemplary attenuating mutations include an attenuating insertion mutation following amino acid 385 of the S.A.AR86 nsP3 protein. Preferably, the insertion comprises an insertion of at least 2, 4, 6, 8, 10, 12, 14, 16 or 20 amino acids. In embodiments of the invention, the inserted amino acid sequence is rich in serine and threonine residues (e.g., comprises at least 2, 4, 6, or 8 such sites) that serve as a substrate for phosphorylation by serine/threonine kinases.

Preferably, the attenuating mutation comprising insertion of the amino acid sequence Ile-Thr-Ser-Met-Asp-Ser-Trp-Ser-Gly-Pro-Ser-Ser-Leu-Glu-Ile-Val-Asp (SEQ ID NO:1) following amino acid 385 of nsP3 (i.e., the first amino acid is designated as amino acid 386 in nsP3). In other embodiments of the invention, the insertion mutation comprises insertion of a fragment of SEQ ID NO:1 that results in an attenuated phenotype. Preferably, the fragment comprises at least 4, 6, 8, 10, 12, 14 or 16 contiguous amino acids from SEQ ID NO:1.

Those skilled in the art will appreciate that other attenuating insertion sequences comprising a fragment of the sequence set forth above, or which incorporate conservative amino acid substitutions into the sequence set forth above, may be routinely identified by those of ordinary skill in the art (as described above). While not wishing to be bound by any theory of the invention, it appears that the insertion sequence of SEQ ID NO:1 is highly phosphorylated at serine residues, which confers an attenuated phenotype. Thus, other attenuating insertion sequences which serve as substrates for serine (or threonine) phosphorylation may be identified by conventional techniques known to those skilled in the art.

Alternatively, or additionally, there is a Tyr→Ser substitution at amino acid 385 of the S.A.AR86 nsP3 (i.e., just prior to the insertion sequence above). This sequence is conserved in the non-virulent Sindbis-group viruses, but is deleted from S.A.AR86.

Other attenuating mutations for S.A.AR86 include attenuating mutations at those positions that diverge between S.A.AR86 and non-neurovirulent Sindbis group viruses, including attenuating mutations at nsP2 amino acid position 256 (preferably Arg→Ala), 648 (preferably Ile→Val) or 651 (preferably Lys→Glu), attenuating mutations at nsP3 amino acid position 344 (preferably Gly→Glu), 441 (preferably Asp→Gly) or 445 (preferably Ile→Met), attenuating mutations at E2 amino acid position 243 (preferably Ser→Leu), attenuating mutations at 6K amino acid position 30 (preferably Val→Ile), and attenuating mutations at E1 amino acid positions 112 (preferably Val→Ala) or 169 (preferably Leu→Ser).

Alphavirus vectors may advantageously, and preferably, contain two or more attenuating mutations. In particular embodiments of the invention, the alphavirus comprises a S.A.AR86 genomic RNA (e.g., a S.A.AR86 replicon RNA) and comprises two or more attenuating mutations in the nonstructural and/or structural proteins. In embodiments of the invention, at least one of the attenuating mutations is at S.A.AR86 nsP1 amino acid position 538. The alphavirus may further preferably comprise an attenuating mutation that results in a termination codon (e.g., an opal termination codon) at S.A.AR86 amino acid position nsP3 537.

S.A.AR86 vectors (or S.A.AR86 chimeric vectors) containing the attenuating mutations above may be double-helper vectors or replicon vectors as disclosed in U.S. Pat. No. 5,639,650 (the disclosure of which is incorporated herein in its entirety by reference) and WO 96/37616, U.S. Pat. No. 5,792,462 and U.S. Pat. No. 6,156,558 to Johnston et al. (the disclosures of which are incorporated herein in their entirety by reference).

The complete genomic sequence of S.A.AR86 is available (Simpson et al., (1996) *Virology* 222:464; U.S. Pat. Nos. 5,639,650; 5,811,407; GenBank accession number 146902; the disclosures of which are incorporated herein by reference in their entireties). The coding regions of the structural and nonstructural coding sequences are known in the art. Referring to GenBank accession number 146902, nucleotides 1 through 59 represent the 5' untranslated region (UTR), the non-structural polyprotein is encoded by nucleotides 60 through 7559 (nsP1-nt60 through nt1679; nsP2-nt1680 through nt4099; nsP3-nt4100 through nt5729; nsP4-nt5730 through nt7559), the structural polyprotein is encoded by nucleotides 7608 through 11342 (capsid-nt7608 through nt8399; E3-nt8400 through nt8591; E2-nt8592 through nt9860; 6K-nt9861 through nt10025; E1-nt10026 through nt11342), and the 3' UTR is represented by nucleotides 11346 through 11663.

Mutations may be introduced into the alphavirus vector by any method known in the art. For example, mutations may be introduced into the alphavirus RNA by performing site-directed mutagenesis on the cDNA which encodes the RNA, in accordance with known procedures (see, Kunkel, *Proc. Natl. Acad. Sci. USA* 82, 488 (1985), the disclosure of which is incorporated herein by reference in its entirety). Alternatively, mutations may be introduced into the RNA by replacement of homologous restriction fragments in the cDNA which encodes for the RNA, in accordance with known procedures.

III. Capsid Enhancer Sequences.

The present invention also provides isolated nucleotide sequences encoding a S.A.AR86 capsid enhancer sequence that enhances transcription and translation of sequences operatively associated therewith. The present invention also provides alphavirus replicon and helper constructs comprising a S.A.AR86 capsid enhancer sequence. Alternatively, the present invention provides S.A.AR86 replicon and helper constructs comprising a capsid enhancer sequence from another alphavirus (e.g., from Sindbis or Semliki Forest virus; see, U.S. Pat. No. 6,224,879 to Sjoberg et al., Smerdou et al., (1999) *J. Virology* 73:1092; Frolov et al., (1996) *J. Virology* 70:1182; the disclosures of which are incorporated herein in their entireties).

The S.A.AR86 capsid enhancer sequence comprises sequences within the 5' non-coding and/or 5' coding sequences (preferably, the 5' coding sequences) of the S.A.AR86 capsid protein that enhance expression (e.g., transcription and translation) of sequences operatively associated therewith. Preferably, the capsid enhancer sequence includes the sequences containing the S.A.AR86 26S subgenomic promoter. It is also preferred that the capsid enhancer sequence contains the 5' coding sequences at about nucleotides 77 to 139 of the viral 26S RNA (coding sequence for amino acids 9–30 of the capsid protein), which form a hairpin structure.

Accordingly, the capsid enhancer sequence more preferably contains at least about 50, 75, 100, 150, 200, 300 or more nucleotides from the 5' coding sequence for the S.A.AR86 capsid protein, including the hairpin structure. In other preferred embodiments, the capsid enhancer sequence comprises the S.A.AR86 26S subgenomic promoter sequence and about 50, 75, 100, 150, 200, 300 or more nucleotides from the 5' coding sequence for the S.A.AR86 capsid protein. Those skilled in the art will appreciate that modifications may be made in the 5' coding sequences from the capsid protein without substantially reducing its enhancing activities (see, e.g., Frolov et al., (1994) *J. Virology* 70:1182; Frolov et al., (1994) *J. Virology* 68:8111). Preferably, such mutations substantially preserve the RNA hairpin structure formed by the 5' capsid coding sequences.

In other embodiments, the capsid enhancer sequence does not contain all of the 5' coding sequences of the capsid protein that are upstream of the hairpin structure.

The capsid enhancer sequence may encode all or part of the capsid protein. Typically, however, the capsid enhancer region will not encode the entire S.A.AR86 capsid protein. In embodiments of the invention, the capsid enhancer sequence will encode an amino terminal fragment from the S.A.AR86 capsid protein. In those embodiments in which an otherwise functional capsid is encoded by the capsid enhancer sequence, it may be desirable to ablate the capsid autoprotease activity (e.g., as described above).

Alternatively, the capsid enhancer sequence may be derived from the homologous 5' regions of the capsid genes from other alphaviruses, including Sindbis, Semliki Forest Virus, GirdwoodS.A., Ockelbo and Ross River virus.

As a further alternative, the capsid enhancer sequence may be any other sequence that forms an RNA hairpin and which acts to enhance translation of RNA sequences operatively associated therewith.

The present invention also provides a S.A.AR86 genomic RNA that comprises one or more heterologous nucleotide sequences and an alphavirus capsid enhancer sequence that is operatively associated with the heterologous nucleotide sequence(s) such that expression of the sequence(s) is enhanced as compared with expression in the absence of the capsid enhancer sequence. In particular embodiments of the invention, the capsid enhancer sequence is a S.A.AR86 capsid enhancer sequence (as described above). Typically, the capsid enhancer sequence will be 5' to the heterologous nucleotide sequence(s), and the genomic RNA expresses a fusion protein comprising the polypeptide encoded by the capsid enhancer sequence and the polypeptide encoded by the transgene(s).

In particular embodiments of the invention, the S.A.AR86 genomic RNA is a replicon molecule that does not encode the S.A.AR86 capsid protein. The S.A.AR86 replicon contains an alphavirus capsid enhancer sequence (e.g., a S.A.AR86 capsid enhancer sequence) operatively associated with one or more heterologous nucleotide sequences.

In embodiments of the invention, the genomic RNA further encodes a an exogenous protease that will cleave the fusion protein.

Any suitable exogenous protease may be used, as long as it is expressed and acts to cleave the polypeptide(s) encoded by the heterologous nucleotide sequence from the protease and any capsid protein sequence. Additional amino acid sequence(s) may be inserted into the fusion protein, typically between the protease and the polypeptide encoded by the transgene, to provide a suitable cleavage site for the protease. In other embodiments of the invention, the exogenous protease is an autoprotease, thereby eliminating the need to add a protease recognition site into the fusion protein.

One preferred and exemplary exogenous autoprotease is a foot and mouth disease virus 2A autoprotease.

Accordingly, in embodiments of the invention, the present invention provides a S.A.AR86 genomic RNA comprising an alphavirus capsid enhancer sequence (preferably, a S.A.AR86 capsid enhancer sequence), a segment encoding an autoprotease, and one or more heterologous nucleotide sequences. Alternatively, the genomic RNA may encode a protease and a protease recognition site, i.e., if an autoprotease is not used. Typically, the genomic RNA will comprise in the 5' to 3' direction, the alphavirus capsid enhancer sequence, the segment encoding the autoprotease (or a protease and the appropriate protease cleavage site), and the heterologous nucleotide sequence(s).

Different configurations of the heterologous nucleotide sequence(s), the capsid enhancer sequence, and the sequence encoding the exogenous protease may be employed as long as the capsid enhancer sequence augments expression of the heterologous nucleotide sequence(s), as compared with the level seen in the absence of the capsid enhancer sequence. These sequences will typically be configured so that the polypeptide encoded by the heterologous nucleotide sequence can be released from the protease and any capsid protein sequence after cleavage by the protease.

In other embodiments, the present invention provides an isolated nucleotide sequence comprising an alphavirus capsid enhancer sequence (e.g., a S.A.AR86 capsid enhancer sequence) operably associated with the alphavirus (e.g., S.A.AR86) glycoprotein coding sequences. The isolated nucleotide sequence containing the capsid enhancer sequence may encode the S.A.AR86 E1 and/or E2 glycoproteins. In one particular embodiment, the isolated nucleotide sequence encodes both the E1 and E2 glycoproteins. Alternatively, the glycoproteins are expressed from different nucleic acid molecules (e.g., different helpers), one or both of which comprise a capsid enhancer sequence.

The isolated nucleotide sequence may further comprise a segment encoding an exogenous protease (and protease cleavage recognition site if not an autoprotease), as described above. In other preferred embodiments, the E1 and E2 glycoproteins are expressed from two separate isolated nucleic acid sequences, each comprising the capsid enhancer sequence and, optionally, the segment encoding the exogenous protease, as described above.

Typically, the isolated nucleotide sequence comprising the S.A.AR86 capsid enhancer sequence, the optional segment encoding the exogenous protease, and the alphavirus glycoprotein coding sequence(s) will be used as a helper for packaging propagation-defective alphavirus vectors. This isolated nucleotide sequence may be advantageously employed as a helper in split-helper systems for expressing one or more of the alphavirus glycoproteins (preferably, S.A.AR86 glycoproteins) in trans from the alphavirus capsid protein. Typically and preferably, the isolated nucleotide sequence will not contain an alphavirus packaging signal.

The helper may be RNA, DNA or an RNA/DNA chimera, as is known in the art. The helper may be provided to the packaging cell as an RNA molecule (e.g., by electroporation or lipofection). Alternatively, the helper may be a DNA molecule that is stably integrated into the genome of a packaging cell or is introduced as a non-integrating DNA vector (e.g., a plasmid) as is known in the art.

As still a further aspect, the present invention provides an isolated nucleotide sequence comprising a S.A.AR86 capsid enhancer sequence and a segment encoding an alphavirus glycoprotein (e.g., the E1 and/or E2 glycoproteins). The alphavirus glycoprotein coding sequences may be from any suitable alphavirus, including Ockelbo, Girdwood, Sindbis, Semliki Forest virus, Ross River Virus, or S.A.AR86, as long as expression of the sequences is enhanced by the S.A.AR86 capsid enhancer sequence as compared with the level of expression in the absence thereof. The isolated nucleotide sequence may further comprise a segment encoding an exogenous protease (and a protease recognition site if not an autoprotease), as described above.

The present invention further provides isolated polypeptides encoded by the isolated nucleotide sequences described above.

The isolated nucleotide sequences containing the capsid enhancer sequence may additionally contain one or more attenuating mutations in the structural or nonstructural proteins (as described herein).

IV. Helper Cells and Methods of Producing Replicon Particles.

Another aspect of the present invention is a helper cell and methods for producing propagation-incompetent alphavirus replicon particles, preferably S.A.AR86 replicon particles or chimeric replicon particles comprising S.A.AR86 structural proteins or a S.A.AR86 replicon RNA.

The helper cells of the invention contain one or more helper sequences (i.e., as DNA and/or RNA molecules) encoding the alphavirus structural proteins (e.g., S.A.AR86 structural proteins). In other embodiments of the invention, the helper cell further comprises one or more replicon molecules each comprising one or more heterologous nucleotide sequences, as described herein.

Typically, the helper sequences will not include an alphavirus packaging sequence, whereas the replicon will contain an alphavirus packaging sequence (e.g., a S.A.AR86 packaging sequence).

The helper cells are typically alphavirus-permissive cells. Alphavirus-permissive cells employed in the methods of the present invention are cells that, upon transfection with the viral RNA transcript, are capable of producing viral particles. Preferred alphavirus-permissive cells are TR339-permissive cells, Girdwood S.A.-permissive cells, S.A.AR86-permissive cells, and Ockelbo-permissive cells. Alphaviruses have a broad host range. Examples of suitable host cells include, but are not limited to Vero cells, baby hamster kidney (BHK) cells, and chicken embryo fibroblast cells.

As described hereinabove, genes encoding the alphavirus structural proteins are distributed among one or more helper molecules (preferably, two or three helper RNAs). In addition, one or more structural proteins may be encoded by the replicon RNA, provided that the replicon RNA does not encode at least one structural protein such that the resulting alphavirus particle is propagation defective in the absence of the helper sequence(s).

It is further preferred that at least one of the alphavirus structural and/or non-structural proteins encoded by the replicon and helper molecules contain one or more attenuating mutations.

The helper sequences and/or replicon may further comprise an alphavirus capsid enhancer sequence (e.g., a S.A.AR86 capsid enhancer sequence), as described above.

In one particular embodiment, the replicon molecule encodes at least one, but not all, of the alphavirus structural proteins (e.g., the E1 and/or ±2 glycoproteins and/or the capsid protein). According to this embodiment, it is preferred that the replicon encodes the capsid protein, and the E1 and E2 glycoproteins are encoded by one or more separate helper molecules. It is preferred that the glycoproteins are encoded by two separate helper molecules, so as to minimize the possibility of recombination to produce replication-competent virus.

In another preferred embodiment, the replicon does not encode any of the E1 glycoprotein, the E2 glycoprotein, or the capsid protein. According to this embodiment, the capsid protein and alphavirus glycoproteins are encoded by one or more helper molecules, preferably two or more helper molecules. By distributing the coding sequences for the structural proteins among two, three or even more helper molecules, the likelihood that recombination will result in replication-competent virus is reduced.

In a further embodiment, the replicon does not encode any of the alphavirus structural proteins.

As described above, the replicon may not encode the structural protein(s) because of a partial or complete deletion of the coding sequence(s) or otherwise contains a mutation that prevents the expression of a functional protein(s). In embodiments of the invention, all or substantially all of the coding sequences for the structural protein(s) that is not encoded by the replicon are deleted from the replicon molecule.

In one preferred embodiment, the E1 and E2 glycoproteins are encoded by one helper molecule, and the capsid protein is encoded by another helper molecule. In another preferred embodiment, the E1 glycoprotein, E2 glycoprotein, and capsid protein are each encoded by separate helper molecules. In other embodiments, the capsid protein and one of the glycoproteins are encoded by one helper molecule, and the other glycoprotein is encoded by a second helper molecule.

It is preferred that duplicate copies of the structural proteins are not present among the replicon and helper molecules. If duplicate copies of the structural proteins are present, generally other approaches are used to avoid recombination events and/or generation of replication-competent virus.

The combined expression of the replicon molecule and the one or more helper molecules in the packaging cell results in the production of an assembled alphavirus particle comprising a replicon RNA packaged within alphavirus structural proteins, which is able to infect a cell, but is unable to produce a productive infection (i.e., produce new virus particles).

Accordingly, in particular preferred embodiments, the present invention provides a helper cell for expressing an infectious, propagation-defective, alphavirus particle, comprising, in an alphavirus permissive cell: (a) one or more isolated nucleotide sequences encoding a S.A.AR86 E1 glycoprotein and a S.A.AR86 E2 glycoprotein. The packaging cell may further comprise an isolated nucleotide sequence encoding a S.A.AR86 capsid protein and/or a replicon molecule.

As another preferred embodiment, the present invention provides a helper cell for expressing an infectious, propagation defective, alphavirus particle, comprising, in an alphavirus permissive cell: (a) an isolated nucleotide sequence encoding a S.A.AR86 E1 glycoprotein and a S.A.AR86 E2 glycoprotein. The helper cell may further comprise an isolated nucleotide sequence encoding a S.A.AR86 capsid protein and/or a replicon molecule.

As a further aspect, the present invention provides a method of making infectious, propagation defective, alphavirus replicon particles using the helper cells, helper sequences, and replicons described herein.

In one particular embodiment, the present invention provides a method of making infectious, defective, alphavirus replicon particles, comprising: (a) providing a helper cell, comprising: (i) one or more helper sequences encoding a S.A.AR86 E1 glycoprotein, a S.A.AR86 E2 glycoprotein, and a S.A.AR86 capsid protein, (ii) an alphavirus replicon molecule, wherein the replicon molecule comprises an alphavirus packaging signal and one or more heterologous nucleotide sequence(s), wherein the combined expression of the replicon molecule, the one or more isolated nucleotide sequences encoding the S.A.AR86 E1 and E2 glycoproteins and the S.A.AR86 capsid protein produces an assembled alphavirus particle which comprises one or more heterologous nucleotide sequence(s), is able to infect a cell, and is unable to produce new virus particles in the absence of helper sequences; (b) producing alphavirus particles in the packaging cell; and (c) collecting the alphavirus particles from the packaging cell.

In another preferred embodiment, the invention provides a method of making infectious, defective, alphavirus replicon particles, comprising: (a) providing a helper cell, comprising: (i) an alphavirus replicon molecule, wherein the replicon molecule comprises an alphavirus packaging signal, one or more heterologous nucleotide sequence(s), and a segment encoding one but not all of the alphavirus capsid protein, the alphavirus E1 glycoprotein, and the alphavirus E2 glycoprotein, (ii) one or more helper sequences encoding the alphavirus structural protein(s) not encoded by the replicon molecule; wherein the combined expression of the replicon molecule and the one or more helper sequences produces an assembled alphavirus particle which comprises one or more heterologous nucleotide sequence(s), is able to infect a cell, and is unable to produce new virus particles in the absence of the helper sequence(s); (b) producing alphavirus particles in the packaging cell; and (c) collecting the alphavirus particles from the packaging cell.

Preferably, the population of alphavirus particles contains no detectable-replication competent alphavirus particles. Replication-competent virus may be detected by any method known in the art, e.g., by neurovirulence following intracerebral injection into suckling mice, or by passage twice on alphavirus-permissive cells (e.g., BHK cells) and evaluation for virus induced cytopathic effects.

Preferably, the helper and replicon molecules are RNA molecules that are introduced into the cell, e.g., by lipofection or electroporation. Uptake of helper RNA and replicon RNA molecules into packaging cells in vitro can be carried out according to any suitable means known to those skilled in the art. Uptake of RNA into the cells can be achieved, for example, by treating the cells with DEAE-dextran, treating the RNA with LIPOFECTIN™ before addition to the cells, or by electroporation, with electroporation being the currently preferred means. These techniques are well known in the art. See e.g., U.S. Pat. No. 5,185,440 to Davis et al., and PCT Publication No. WO 92/10578 to Bioption AB, the disclosures of which are incorporated herein by reference in their entirety.

Alternatively, one or all of the helper and/or replicon molecules are DNA molecules, which are preferably stably integrated into the genome of the helper cell. The DNA molecule may be any vector known in the art, including but not limited to a non-integrating DNA vector, such as a plasmid, or a viral vector.

The production of the infectious viral particles in the helper cells may be carried out using conventional techniques known in the art. See e.g., U.S. Pat. No. 5,185,440 to Davis et al., and international patent publication No. WO 92/10578 to Bioption AB.

V. Recombinant Alphavirus Vectors.

According to embodiments of the invention, it is desirable to employ an alphavirus vector that encodes one or more (e.g., two, three, four, five, etc.) heterologous nucleic acid sequences, preferably each encoding an antigen according to the present invention. In particular embodiments, wherein there are two or more heterologous nucleotide sequences, each heterologous nucleic acid sequence will typically be operably associated with a promoter. Alternatively, an internal ribosome entry site (IRES) sequence(s) can be placed downstream of a promoter and upstream of the heterologous nucleic acid sequence(s). The heterologous nucleic acid sequences can be associated with a constitutive or inducible promoter. An alphavirus 26S subgenomic promoter is preferred. In general, the S.A.AR86 26S subgenomic promoter is preferred with S.A.AR86 replication proteins, and the VEE 26S subgenomic promoter is preferred with VEE replication proteins, and the like.

Heterologous nucleic acids of interest include nucleic acids encoding peptides and proteins, preferably immunogenic (e.g., for an immunogenic composition or a vaccine) or therapeutic (e.g., for medical or veterinary uses) polypeptides.

An "immunogenic" polypeptide, or "immunogen" as used herein is any polypeptide that elicits an immune response in a subject, more preferably, the immunogenic polypeptide is suitable for providing some degree of protection to a subject against a disease. The present invention may be employed to express an immunogenic polypeptide in a subject (e.g., for vaccination) or for immunotherapy (e.g., to treat a subject with cancer or tumors).

An immunogenic polypeptide, or immunogen, may be any polypeptide suitable for protecting the subject against a disease, including but not limited to microbial, bacterial, protozoal, parasitic, and viral diseases. For example, the immunogen may be an orthomyxovirus immunogen (e.g., an influenza virus immunogen, such as the influenza virus hemagglutinin (HA) surface protein or the influenza virus nucleoprotein gene, or an equine influenza virus immunogen), or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, pol and env genes products). The immunogen may also be an arenavirus immunogen (e.g., Lassa fever virus immunogen, such as the Lassa fever virus nucleocapsid protein gene and the Lassa fever envelope glycoprotein gene), a Picornavirus immunogen (e.g., a Foot and Mouth Disease virus immunogen), a poxvirus immunogen (e.g., vaccinia, such as the vaccinia L1 or L8 genes), an Orbivirus immunogen (e.g., an African horse sickness virus immunogen), a flavivirus immunogen (e.g., a yellow fever virus immunogen, a West Nile virus immunogen, or a Japanese encephalitis virus immunogen), a filovirus immunogen (e.g., an Ebola virus immunogen, or a Marburg virus immunogen, such as NP and GP genes), a bunyavirus immunogen (e.g., RVFV, CCHF, and SFS immunogens), or a coronavirus immunogen (e.g., an infectious human coronavirus immunogen, such as the human coronavirus envelope glycoprotein gene, or a porcine transmissible gastroenteritis virus immunogen, or an avian infectious bronchitis virus immunogen). The immunogen may further be a polio antigen, herpes antigen (e.g., CMV, EBV, HSV antigens) mumps antigen, measles antigen, rubella antigen, diptheria toxin or other diptheria antigen, pertussis antigen, hepatitis (e.g., hepatitis A or hepatitis B) antigen, or any other vaccine antigen known in the art.

The present invention may also be advantageously employed to produce an immune response against chronic or latent infective agents, which typically persist because they fail to elicit a strong immune response in the subject. Illustrative latent or chronic infective agents include, but are not limited to, hepatitis B, hepatitis C, Epstein-Barr Virus, herpes viruses, human immunodeficiency virus, and human papilloma viruses. Alphavirus vectors encoding antigens from these infectious agents may be administered to a cell or a subject according to the methods described herein.

Alternatively, the immunogen may be any tumor or cancer cell antigen. Preferably, the tumor or cancer antigen is expressed on the surface of the cancer cell. Exemplary cancer antigens for specific breast cancers are the HER2 and BRCA1 antigens. Other illustrative cancer and tumor cell antigens are described in S. A. Rosenberg, (1999) *Immunity* 10:281) and include, but are not limited to: MART-1/MelanA, gp100, tyrosinase, TRP-1, TRP-2, MAGE1, MAGE-3, GAGE-1/2, BAGE, RAGE, NY-ESO-1, CDK-4, β-catenin, MUM-1, Caspase-8, KIAA0205, HPVE&, SART-1, PRAME, p15, and p53 antigens.

The immunogen may also be a "universal" or "artificial" cancer or tumor cell antigen as described in international patent publication WO 99/51263, which is hereby incorporated by reference in its entirety.

Preferably, administration of an alphavirus virus comprising one or more heterologous nucleotide sequences encoding an immunogen elicits an active immune response in the subject, more preferably a protective immune response (each as defined below).

The term "cancer" has its understood meaning in the art, for example, an uncontrolled growth of tissue that has the potential to spread to distant sites of the body (i.e., metastasize). Exemplary cancers include, but are not limited to, leukemias, lymphomas, colon cancer, renal cancer, liver cancer, breast cancer, lung cancer, prostate cancer, ovarian cancer, melanoma, and the like. Other illustrative cancers include cancers of the bone and bone marrow. Preferred are methods of treating and preventing tumor-forming cancers. The term "tumor" is also understood in the art, for example, as an abnormal mass of undifferentiated cells within a multicellular organism. Tumors can be malignant or benign. Preferably, the inventive methods disclosed herein are used to prevent and treat malignant tumors.

Cancer and tumor antigens according to the present invention have been described hereinabove. Alphaviruses encoding cancer or tumor antigens may be administered in methods of treating cancer or tumors, respectively.

By the terms "treating cancer" or "treatment of cancer", it is intended that the severity of the cancer is reduced or the cancer is at least partially eliminated. Preferably, these terms indicate that metastasis of the cancer is reduced or at least partially eliminated. It is further preferred that these terms indicate that growth of metastatic nodules (e.g., after surgical removal of a primary tumor) is reduced or at least partially eliminated. By the terms "prevention of cancer" or "preventing cancer" it is intended that the inventive methods at least partially eliminate or reduce the incidence or onset of cancer. Alternatively stated, the present methods slow, control, decrease the likelihood or probability, or delay the onset of cancer in the subject.

Likewise, by the terms "treating tumors" or "treatment of tumors", it is intended that the severity of the tumor is reduced or the tumor is at least partially eliminated. Preferably, these terms are intended to mean that metastasis of the tumor is reduced or at least partially eliminated. It is also preferred that these terms indicate that growth of metastatic nodules (e.g., after surgical removal of a primary tumor) is reduced or at least partially eliminated. By the terms "prevention of tumors" or "preventing tumors" it is intended that the inventive methods at least partially eliminate or reduce the incidence or onset of tumors. Alternatively stated, the present methods slow, control, decrease the likelihood or probability, or delay the onset of tumors in the subject.

It is known in the art that immune responses may be enhanced by immunomodulatory cytokines (e.g., α-interferon, β-interferon, γ-interferon, ω-interferon, τ-interferon, interleukin-1α, interleukin-1β, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, and lymphotoxin). Accordingly, in particular embodiments of the invention, immunomodulatory cytokines (preferably, CTL inductive cytokines) are administered to a subject in conjunction with the methods described herein for producing an immune response or providing immunotherapy.

Cytokines may be administered by any method known in the art. Exogenous cytokines may be administered to the subject, or alternatively, a nucleotide sequence encoding a cytokine may be delivered to the subject using a suitable vector, and the cytokine produced in vivo. In preferred embodiments, an alphavirus vector encoding a cytokine is used to deliver the cytokine to the subject.

The present invention further finds use in methods of producing antibodies in vivo for passive immunization techniques. According to this embodiment an alphavirus vector expressing an immunogen of interest is administered to a subject, as described herein by direct administration or ex vivo cell manipulation techniques. The antibody may then be collected from the subject using routine methods known in the art. The invention further finds use in methods of producing antibodies against an immunogen expressed from an alphavirus vector for any other purpose, e.g., for diagnostic purpose or for use in histological techniques.

Alternatively, the present invention may be practiced to express a therapeutic polypeptide in the cell, in vitro or in vivo. A "therapeutic" polypeptide is a polypeptide that may alleviate or reduce symptoms that result from an absence or defect in a protein in a cell or subject. Alternatively, a "therapeutic" polypeptide is one that otherwise confers a benefit to a subject, e.g., anti-cancer effects.

Therapeutic peptides and proteins include, but are not limited to, CFTR (cystic fibrosis transmembrane regulator protein), dystrophin (including the protein product of dystrophin mini-genes, see, e.g., Vincent et al., (1993) *Nature Genetics* 5:130), utrophin (Tinsley et al., (1996) *Nature* 384:349), clotting factors (Factor XIII, Factor IX, Factor X, etc.), erythropoietin, the LDL receptor, lipoprotein lipase, ornithine transcarbamylase, β-globin, α-globin, spectrin, α-antitrypsin, adenosine deaminase, hypoxanthine guanine phosphoribosyl transferase, β-glucocerebrosidase, sphingomyelinase, lysosomal hexosamimidase, branched-chain keto acid dehydrogenase, hormones, growth factors (e.g., insulin-like growth factors 1 and 2, platelet derived growth factor, epidermal growth factor, nerve growth factor, neurotrophic factor −3 and −4, brain-derived neurotrophic factor, glial derived growth factor, transforming growth factor-α and -β, and the like), cytokines (e.g., α-interferon, β-interferon, γ-interferon, ω-interferon, τ-interferon, interleukin-1α, interleukin-1β, interleukin-2, interleukin-3, interleukin-4, interleukin 5, interleukin-6, interleukin-7, interleukin-8, interleukin-9, interleukin-10, interleukin-10, interleukin-11, interleukin 12, interleukin-13, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, lymphotoxin), suicide gene products (e.g., herpes simplex virus thymidine kinase, cytosine deaminase, diphtheria toxin, cytochrome P450, deoxycytidine kinase, and tumor necrosis factor), proteins conferring resistance to a drug used in cancer therapy, tumor suppressor gene products (e.g., p53, Rb, Wt-1, NF1, VHL, APC, and the like), and any other polypeptide that has a therapeutic effect in a subject in need thereof.

Further exemplary therapeutic polypeptides include those that may used in the treatment of a disease condition including, but not limited to, cystic fibrosis (and other diseases of the lung), hemophilia A, hemophilia B, thalassemia, anemia and other blood disorders, AIDS, Alzheimer's disease, Parkinson's disease, Huntington's disease, amylotrophic lateral sclerosis, epilepsy, and other neurological disorders, cancer, diabetes mellitus, muscular dystrophies (e.g., Duchenne, Becker), Gaucher's disease, Hurler's disease, adenosine deaminase deficiency, glycogen storage diseases and other metabolic defects, retinal degenerative diseases (and other diseases of the eye), and diseases of solid organs (e.g., brain, liver, kidney, heart).

The present invention may be preferably, and advantageously, employed for relatively short-term therapeutic regimes. For example, immunomodulators (e.g., cytokines, as defined above) may be delivered using an alphavirus vector as described herein. Likewise, supportive therapeutic agents (e.g., immunomodulators, erythropoietin) may be provided in conjunction with chemotherapy.

As a further alternative, the alphavirus vector may be used to express an antibody against a defective or over-expressed protein. Subjects expressing the defective protein or over-expressed protein may be administered an alphavirus vector according to the invention expressing an antibody that modulates the activity of the protein.

As a further alternative, the heterologous nucleic acid sequence may encode a reporter polypeptide (e.g., an enzyme). Reporter proteins are known in the art and include, but are not limited to, Green Fluorescent Protein, β-galactosidase, alkaline phosphatase, chloramphenicol acetyltransferase, and the like.

Alternatively, in particular embodiments of the invention, the nucleic acid of interest may encode an antisense nucleic acid, a ribozyme (e.g., as described in U.S. Pat. No. 5,877,022), RNAs that effect spliceosome-mediated trans-splicing (Puttaraju et al., (1999) Nature Biotech. 17:246), or other non-translated RNAs, such as "guide" RNAs (Gorman et al., (1998) Proc. Nat Acad. Sci. USA 95:4929; U.S. Pat. No. 5,869,248 to Yuan et al.), and the like.

In general, "antisense" refers to the use of small, synthetic oligonucleotides to inhibit gene expression by inhibiting the function of the target mRNA containing the complementary sequence. Milligan, J. F. et al., J. Med. Chem. 36(14), 1923–1937 (1993). Gene expression is inhibited through hybridization to coding (sense) sequences in a specific mRNA target by hydrogen bonding according to Watson-Crick base pairing rules. The mechanism of antisense inhibition is that the exogenously applied oligonucleotides decrease the mRNA and protein levels of the target gene. Milligan, J. F. et al., J. Med. Chem. 36(14), 1923–1937 (1993). See also Helene, C. and Toulme, J., Biochim. Biophys. Acta 1049, 99–125 (1990); Cohen, J. S., Ed., OLIGODEOXYNUCLEOTIDES AS ANTISENSE INHIBITORS OF GENE EXPRESSION, CRC Press: Boca Raton, Fla. (1987).

Antisense oligonucleotides may be of any suitable length, depending on the particular target being bound. The only limits on the length of the antisense oligonucleotide is the capacity of the virus for inserted heterologous RNA. Antisense oligonucleotides may be complementary to the entire mRNA transcript of the target gene or only a portion thereof. Preferably the antisense oligonucleotide is directed to an mRNA region containing a junction between intron and exon. Where the antisense oligonucleotide is directed to an intron/exon junction, it may either entirely overlie the junction or may be sufficiently close to the junction to inhibit splicing out of the intervening exon during processing of precursor mRNA to mature mRNA (e.g., with the 3' or 5' terminus of the antisense oligonucleotide being positioned within about, for example, 10, 5, 3 or 2 nucleotides of the intron/exon junction). Also preferred are antisense oligonucleotides which overlap the initiation codon.

When practicing the present invention, the antisense oligonucleotides administered may be related in origin to the species to which it is administered. When treating humans, human antisense may be used if desired.

The heterologous nucleic acid may be operably associated with expression control elements, such as transcription/translation control signals, origins of replication, polyadenylation signals, and internal ribosome entry sites (IRES), promoters, enhancers, and the like. Those skilled in the art will appreciate that a variety of promoter/enhancer elements may be used depending on the level and tissue-specific expression desired. The promoter/enhancer may be constitutive or inducible, depending on the pattern of expression desired. The promoter/enhancer may be native or foreign and can be a natural or a synthetic sequence.

Promoters/enhancers that are native to the subject to be treated are most preferred. Also preferred are promoters/enhancers that are native to the heterologous nucleic acid sequence. The promoter/enhancer is chosen so that it will function in the target cell(s) of interest. Mammalian promoters/enhancers are also preferred.

Preferably, the heterologous nucleotide sequence is operably associated with a promoter that provides high level expression of the heterologous nucleotide sequence, e.g., an alphavirus subgenomic 26S promoter (preferably, a VEE 26S or S.A.AR 26S subgenomic promoter).

In embodiments of the invention in which the heterologous nucleic acid sequence(s) will be transcribed and then translated in the target cells, specific initiation signals are generally required for efficient translation of inserted protein coding sequences. These exogenous translational control sequences, which may include the ATG initiation codon and adjacent sequences, can be of a variety of origins, both natural and synthetic.

V. DNA Sequences, Vectors and Transformed Cells.

As a further aspect, the present invention provides RNA sequences (e g., cDNA sequences) and vectors encoding infectious S.A.AR86 genomic RNA transcripts according to the present invention. Preferably, the DNA and genomic RNA sequences comprise one or more he otide sequences. Also provided are alphavirus particles containing the genomic RNA transcribed from the DNA molecules.

The present invention further provides vectors comprising a DNA sequence encoding a S.A.AR86 genomic RNA transcript operably associated with a promoter that drives transcription of the DNA sequence. Examples of promoters which are suitable for use with the DNA sequences of the present invention include, but are not limited to T3 promoters, T7 promoters, cytomegalovirus (CMV) promoters, and SP6 promoters.

The DNA sequence may be encoded by any suitable vector known in the art, including but not limited to, plasmids, naked DNA vectors, yeast artificial chromosomes (yacs), bacterial artificial chromosomes (bacs), phage, viral vectors, and the like. Preferably, the vector is a plasmid.

Genomic RNA transcripts may be synthesized from the DNA template by any method known in the art. Preferably, the RNA is synthesized from the DNA sequence in vitro using purified RNA polymerase in the presence of ribonucleotide triphosphates and cap analogs in accordance with conventional techniques. Alternatively, the RNA may be synthesized intracellularly after introduction of the DNA.

Further provided are cells containing the DNA sequences, genomic RNA transcribed from the DNA sequences, and alphavirus vectors of the invention.

The S.A.AR86 DNA constructs, genomic RNA transcripts, and virus particles produced therefrom are useful for the preparation of pharmaceutical formulations, such as vaccines. In addition, the DNA clones, genomic RNA transcripts, and infectious viral particles of the present invention are useful for administration to animals for the purpose of producing antibodies to S.A.AR86, which antibodies may be collected and used in known diagnostic techniques for the detection of S.A.AR86. Antibodies can also be generated to the viral proteins expressed from the DNAs disclosed herein. As another aspect of the present invention, the claimed DNA clones are useful as nucleotide probes to detect the presence of S.A.AR86 transcripts.

VI. Gene Transfer Technology.

The methods of the present invention provide a means for delivering heterologous nucleic acid sequences into a broad range of host cells. The vectors and other reagents, methods and pharmaceutical formulations of the present invention are additionally useful in a method of administering a polypeptide to a subject in need thereof, as a method of treatment or otherwise. In this manner, the polypeptide may thus be produced in vivo in the subject. The subject may be in need of the polypeptide because the subject has a deficiency of the polypeptide, or because the production of the polypeptide in the subject may impart some therapeutic effect, as a method of treatment or otherwise, and as explained further below.

In general, the present invention may be employed to deliver any foreign nucleic acid with a biological effect to treat or ameliorate the symptoms associated with any disorder related to gene expression. Illustrative disease states include, but are not limited to: cystic fibrosis (and other diseases of the lung), hemophilia A, hemophilia B, thalassemia, anemia and other blood disorders, AIDS, Alzheimer's disease, Parkinson's disease, Huntington's disease, amyotrophic lateral sclerosis, epilepsy, and other neurological disorders, cancer, diabetes mellitus, muscular dystrophies (e.g., Duchenne, Becker), Gaucher's disease, Hurler's disease, adenosine deaminase deficiency, glycogen storage diseases and other metabolic defects, retinal degenerative diseases (and other diseases of the eye), diseases of solid organs (e.g., brain, liver, kidney, heart), and the like.

Gene transfer has substantial potential use in understanding and providing therapy for disease states. There are a number of inherited diseases in which defective genes are known and have been cloned. In some cases, the function of these cloned genes is known. In general, the above disease states fall into two classes: deficiency states, usually of enzymes, which are generally inherited in a recessive manner, and unbalanced states, at least sometimes involving regulatory or structural proteins, which are inherited in a dominant manner. For deficiency state diseases, gene transfer could be used to bring a normal gene into affected tissues for replacement therapy, as well as to create animal models for the disease using antisense mutations. For unbalanced disease states, gene transfer could be used to create a disease state in a model system, which could then be used in efforts to counteract the disease state. Thus the methods of the present invention permit the treatment of genetic diseases. As used herein, a disease state is treated by partially or wholly remedying the deficiency or imbalance that causes the disease or makes it more severe. The use of site-specific integration of nucleic sequences to cause mutations or to correct defects is also possible.

The instant invention may also be employed to provide an antisense nucleic acid to a cell in vitro or in vivo. Expression of the antisense nucleic acid in the target cell diminishes expression of a particular protein by the cell. Accordingly, antisense nucleic acids may be administered to decrease expression of a particular protein in a subject in need thereof. Antisense nucleic acids may also be administered to cells in vitro to regulate cell physiology, e.g., to optimize cell or tissue culture systems. The present invention is also useful to deliver other non-translated RNAs, e.g., ribozymes (e.g., as described in U.S. Pat. No. 5,877,022), RNAs that effect spliceosome-mediated trans-splicing (Puttaraju et al., (1999) *Nature Biotech.* 17:246), or "guide" RNAs (see, e.g., Gorman et al., (1998) *Proc. Nat. Acad. Sci. USA* 95:4929; U.S. Pat. No. 5,869,248 to Yuan et al.) to a target cell.

Finally, the instant invention finds further use in diagnostic and screening methods, whereby a gene of interest is transiently or stably expressed in a cell culture system, or alternatively, a transgenic animal model.

VII. Subjects, Pharmaceutical Formulations, Vaccines, and Modes of Administration.

The present invention finds use in both veterinary and medical applications. Suitable subjects include both avians and mammals, with mammals being preferred. The term "avian" as used herein includes, but is not limited to, chickens, ducks, geese, quail, turkeys and pheasants. The term "mammal" as used herein includes, but is not limited to, primates, bovines, ovines, caprines, porcines, equines, felines, canines, lagomorphs, rodents (e.g., rats and mice), etc. Human subjects are the most preferred. Human subjects include fetal, neonatal, infant, juvenile and adult subjects.

In particular embodiments, the present invention provides a pharmaceutical composition comprising an alphavirus vector of the invention in a pharmaceutically-acceptable carrier or other medicinal agents, pharmaceutical agents, carriers, adjuvants, diluents, etc. For injection, the carrier will typically be a liquid. For other methods of administration, the carrier may be either solid or liquid, such as sterile, pyrogen-free water or sterile pyrogen-free phosphate-buffered saline solution. For inhalation administration, the carrier will be respirable, and will preferably be in solid or liquid particulate form. As an injection medium, it is preferred to use water that contains the additives usual for injection solutions, such as stabilizing agents, salts or saline, and/or buffers.

In other embodiments, the present invention provides a pharmaceutical composition comprising a cell that has been infected and genetically modified by an alphavirus vector in a pharmaceutically-acceptable carrier or other medicinal agents, pharmaceutical agents, carriers, adjuvants, diluents, etc. By "pharmaceutically acceptable" it is meant a material that is not biologically or otherwise undesirable, e.g., the material may be administered to a subject without causing any undesirable biological effects. Thus, such a pharmaceutical composition may be used, for example, in transfection of a cell ex vivo or in administering, the alphavirus/antibody compositions or cells directly to a subject.

The cell to be administered the inventive virus vectors can be of any type, including but not limited to neuronal cells (including cells of the peripheral and central nervous systems), retinal cells, epithelial cells (including dermal, gut, respiratory, bladder and breast tissue epithelium), muscle cells (including cardiac, smooth muscle, skeletal muscle, and diaphragm muscle), pancreatic cells (including islet cells), hepatic cells (e.g., parenchyma), fibroblasts, endothelial cells, germ cells, lung cells (including bronchial cells and alveolar cells), prostate cells, stem cells, progenitor cells, dendritic cells, and the like. Alternatively, the cell is a cancer cell (including tumor cells). Moreover, the cells can be from any species of origin, as indicated above.

Alternatively, in embodiments of the invention, the cell is preferably a cell a cell, a bone marrow cell, a cell in the bone-associated connective tissue. Other preferred cells, are cells of the periosteum, endosteum and tendons, generally within the epiphyses of the long bones adjacent to joints.

Cells that may be infected by the alphavirus vectors of the present invention further include, but are not limited to, polymorphonuclear cells, hemopoietic stem cells (including megakaryocyte colony forming units (CFU-M), spleen colony forming units (CFU-S), erythroid colony forming units (CFU-E), erythroid burst forming units (BFU-E), and colony forming units in culture (CFU-C)), erythrocytes, macrophages (including reticular cells), monocytes, granulocytes, megakaryoctyes, lymphocytes, fibroblasts, osteoprogenitor cells, osteoblasts, osteoclasts, marrow stromal cells, chondrocytes and other cells of synovial joints.

The alphavirus vectors of the invention may be administered to elicit an immunogenic response (e.g., as an immunogenic composition or as a vaccine or for immunotherapy). Typically, immunological compositions of the present invention comprise an immunogenic amount of infectious virus particles as disclosed herein in combination with a pharmaceutically-acceptable carrier. An "immunogenic amount" is an amount of the infectious virus particles that is sufficient to evoke an immune response in the subject to which the pharmaceutical formulation is administered. Typically, an amount of about $10^3$ to about $10^{15}$ virus particles, preferably about $10^4$ to about $10^{10}$, and more preferably about $10^4$ to $10^6$ virus particles per dose is suitable, depending upon the age and species of the subject being treated, and the immunogen against which the immune response is desired. Subjects and immunogens are as described above. An alphavirus replicon particle is the preferred alphavirus vector.

The terms "vaccination" or "immunization" are well-understood in the art. For example, the terms vaccination or immunization can be understood to be a process that increases an subject's immune reaction to antigen and therefore the ability to resist or overcome infection. In the case of the present invention, vaccination or immunization may also increase the organism's immune response and resistance to invasion by cancer or tumor cells.

Any suitable vaccine and method of producing an immune response (i.e., immunization) known in the art may be employed in carrying out the present invention, as long as an active immune response (preferably, a protective immune response) against the antigen is elicited.

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to immunogens by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "protective" immune response or "protective" immunity as used herein indicates that the immune response confers some benefit to the subject in that it prevents or reduces the incidence of disease. Alternatively, a protective immune response or protective immunity may be useful in the treatment of disease, in particular cancer or tumors (e.g., by causing regression of a cancer or tumor and/or by preventing metastasis and/or by preventing growth of metastatic nodules). The protective effects may be complete or partial, as long as the benefits of the treatment outweigh any disadvantages thereof.

Vaccination can be by any means known in the art, as described below, but is preferably by parenteral routes (e.g., subcutaneous, intracerebral, intradermal, intramuscular, intravenous, intraarticular), most preferably by subcutaneous injection. The dose of virus is not critical as long as it is sufficient to induce an active immune response to the expressed antigen.

The present invention further provides a method of delivering a nucleic acid to a cell (e.g., to produce an immune response or for therapy). For in vitro methods, the virus may be administered to the cell by standard viral transduction methods, as are known in the art. Preferably, the virus particles are added to the cells at the appropriate multiplicity of infection according to standard transduction methods appropriate for the particular target cells. Titers of virus to administer can vary, depending upon the target cell type and the particular virus vector, and may be determined by those of skill in the art without undue experimentation.

In particular embodiments of the invention, cells are removed from a subject, the alphavirus vector is introduced therein, and the cells are then replaced back into the subject. Methods of removing cells from subject for treatment ex vivo, followed by introduction back into the subject are known in the art. Alternatively, the alphavirus vector is introduced into cells from another subject, into cultured cells, or into cells from any other suitable source, and the cells are administered to a subject in need thereof. Preferably, if the subject's own cells are not used, the cells are HLA compatible with the subject's HLA type. The modified cell may be administered according to a method of ex vivo gene therapy or to provide immunity to a subject (e.g., by introducing a nucleotide sequence encoding an immunogen into an antigen producing cell, such as a dendritic cell).

Dosages of the cells to administer to a subject will vary upon the age, condition and species of the subject, the type of cell, the nucleic acid being expressed by the cell, the mode of administration, and the like. Typically, at least about $10^2$ to about $10^8$, preferably about $10^3$ to about $10^6$ cells, will be administered per dose. Preferably, the cells will be administered in a "immunogenic amount" (as described hereinabove) or a "therapeutically-effective amount".

A "therapeutically-effective" amount as used herein is an amount that is sufficient to alleviate (e.g., mitigate, decrease, reduce) at least one of the symptoms associated with a disease state. Alternatively stated, a "therapeutically-effective" amount is an amount that is sufficient to provide some improvement in the condition of the subject.

A further aspect of the invention is a method of treating subjects in vivo with the inventive alphavirus particles. Administration of the alphavirus particles of the present invention to a human subject or an animal in need thereof can be by any means known in the art for administering virus vectors.

Dosages of the inventive alphavirus particles will depend upon the mode of administration, the disease or condition to be treated, the individual subject's condition, the particular virus vector, and the gene to be delivered, and can be determined in a routine manner. Exemplary doses for achieving therapeutic effects are virus titers of at least about $10^5$, $10^6$, $10^7$, $10^8$, $10^9$, $10^{10}$, $10^{11}$, $10^{12}$, $10^{13}$, $10^{14}$, $10^{15}$ transducing units or more, preferably about $10^8$–$10^{13}$ transducing units.

Exemplary modes of administration for alphavirus vectors according to the present invention include oral, rectal, transmucosal, topical, transdermal, inhalation, parenteral (e.g., intravenous, subcutaneous, intradermal, intramuscular, and intraarticular) administration, and the like, as well as direct tissue or organ injection, alternatively, intrathecal, direct intramuscular, intraventricular, intravenous, intraperitoneal, intranasal, or intraocular injections. Injectables can be prepared in conventional forms, either as liquid solutions or suspensions, solid forms suitable for solution or suspension in liquid prior to injection, or as emulsions. Alternatively, one may administer these reagents in a local rather than systemic manner, for example, in a depot or sustained-release formulation.

In other preferred embodiments, the alphavirus vector is administered intramuscularly, more preferably by intramuscular injection or by local administration (as defined above).

In other preferred embodiments, the alphavirus vectors of the present invention are administered to the lungs. The alphavirus vectors disclosed herein may be administered to the lungs of a subject by any suitable means, but are preferably administered by administering an aerosol suspension of respirable particles comprised of the inventive alphavirus vectors, which the subject inhales. The respirable particles may be liquid or solid. Aerosols of liquid particles comprising the inventive alphavirus vectors may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the inventive virus vectors may likewise be produced with any solid particulate medicament aerosol generator, by techniques known in the pharmaceutical art.

The following examples are provided to illustrate the present invention, and should not be construed as limiting thereof.

EXAMPLE 1

Six week old female CD-1 mice (Charles River Breeding Laboratories; Raleigh, N.C.) were infected intravenously (iv) with $10^3$ pfu of virus derived from the wild-type S.A.AR86 molecular clone ps55 (Simpson et al., (1996) *Virol.* 222:464). Three days post infection, mice were sacrificed and serum was harvested, while the quadriceps muscles, and the femurs (including the knee and hip joints) were removed and placed in PBS supplemented with 1% donor calf serum (Gibco BRL, Grand Island, N.Y.). Muscle tissue was frozen and thawed before homogenization using a mortar and pestle (Kontes Glass Company; Vineland, N.J.), while calcified tissue was crushed using sterile pliers before freeze thaw. The tissue homogenate was then clarified by centrifugation and assayed for infectious virus by plaque assay on BHK-21 cells (ATCC CRL 8544) as previously described (Ryman et al., (2000) *J. Virol.* 74:3366). Virus was consistently isolated from the femurs of infected animals (FIG. 1A). Infectious virus could be isolated from bone and/or joint tissue as early as 24 hours post-inoculation, and up to six days post-inoculation (data not shown). Infectious virus was also detectable in femurs with similar kinetics following intraperitoneal and subcutanaceous inoculation (data not shown). The possibility that the virus detected within the bone/joint tissue was actually due to contamination from serum or surrounding muscle was addressed by measuring virus levels in these tissues. Serum viremia peaked by 24 to 48 hours after iv S.A.AR86 infection (data not shown) and fell below the limit of detection by 72 hours post inoculation (FIG. 1A). Furthermore, comparison of viral titers from perfused and non-perfused animals found no difference in virus levels within the femur on day three post infection (data not shown). Since muscle is a site of Sindbis-group virus replication in suckling mice (Klimstra et al., (1999) *J. Virol.* 73:10387; Trgovcich et al., (1996) *Virol.* 224:73), the level of viral replication within the quadriceps was measured. Unlike neonatal mice, infectious virus was not consistently isolated from adult mouse muscle tissue (FIG. 1A). This suggests that the infectious virus isolated from the femur was due to direct viral replication within bone and/or joint tissue, rather than contamination by virally infected muscle tissue.

EXAMPLE 2

Additional experiments were performed to determine whether bone marrow or calcified/fibroblast connective tissue was the site of virus replication within the hind limb. Adult female CD-1 mice were infected iv with $10^3$ pfu of virus derived from the S.A.AR86 molecular clone ps51, which differs from the wild-type ps55 clone by a single coding change (nsP1 538 Thr to Ile). Three days post infection, the femurs, including the hip and knee joints, were removed and the bone marrow was aspirated and titrated for infectious virus by plaque assay. The remaining tissue, including the diaphysis (barrel) of the femur and the knee and hip joints, was also titrated. Viral titers were at or below the limit of detection in bone marrow aspirates, while the bone/joint tissue had significant levels of virus (FIG. 1B). Comparable results were obtained following infection with virus derived from clone ps55, and no difference in replication within the femur was observed between these two viruses (data not shown). These results suggest that cells tightly associated With calcified/fibroblast connective tissue were the main targets of virus replication.

EXAMPLE 3

Six week old female CD-1 mice were infected iv with $10^3$ pfu of clone s55 or the cloned AR339-like Sindbis-group viruses TR339 (Klimstra et al., (1998) *J. Virol.* 72:7357;

McKnight et al., (1996) *J. Virol.* 70:1981) and TRSB (McKnight et al., (1996) *J. Virol.* 70:1981). Three days post infection, hind limbs were removed and femurs, including the knee and hip joints, were evaluated for the presence of infectious virus by plaque assay. S55, TR339, and TRSB replicated to similar levels within bone/joint tissue (FIG. 1C), suggesting that replication within bone/joint tissue is a general characteristic of Sindbis-group alphaviruses, rather than a specific attribute of S.A.AR86.

Figure 2:
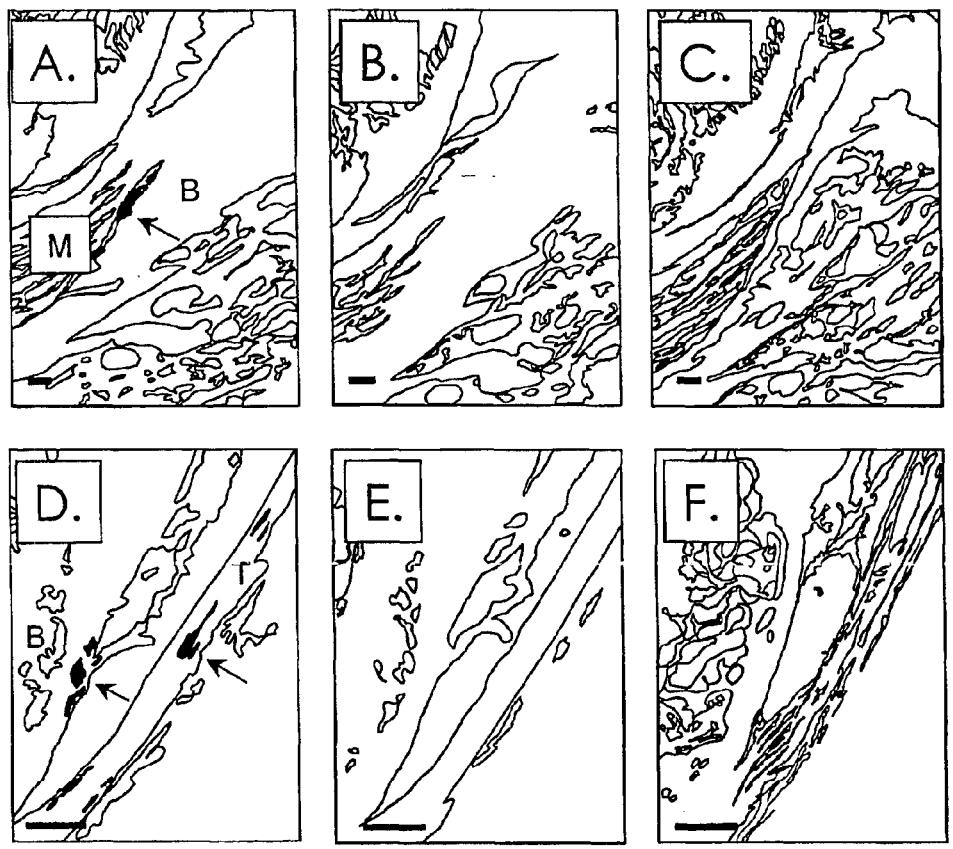
FIG. 2. S.A.AR86 replication within the bone associated connective tissue on the epiphyses (ends) of the long bones. Four to six week old female CD-1 mice were infected iv with $10^3$ or $2.5 \times 10^5$ pfu of s51 or mock infected. Mice were sacrificed at 24 or 48 hours post infection. Following decalcification, 5 uM thick paraffin embedded limb sections were probed with $^{35}$S-labeled riboprobes specific for S.A.AR86 or influenza strain PR/8 HA. A. S.A.AR86 specific in situ signal in periosteum of the tibia 24 hours after infection with 2.5×10⁵ pfu of s51 iv. Muscle is designated by (M), while bone is designated by (B). B. Adjacent section probed with influenza specific riboprobe. C. Adjacent section, H+E staining. D. S.A.AR86 specific in situ signal in tendon and periosteum of the tibia proximal to knee joint 24 hours after infection with 2.5×10⁵ pfu of s51, iv. Tendon is designated by (T) and bone by (B). E. Adjacent section probed with influenza specific riboprobe. F. Adjacent section, H+E staining. Bar=100 microns in each panel.

Crude fractionation studies demonstrated that the majority of infectious S.A.AR86 was found within calcified or fibroblast connective tissue of the femur or joints, while little virus was found in the bone marrow aspirates (FIG. 1B). In order to confirm that bone and/or joint tissue was a target of S.A.AR86 infection and to identify the specific sites of replication within these tissues, in situ hybridization using $^{35}S$ labeled riboprobes specific for S.A.AR86 was performed. Mice were infected iv with either $10^3$ or $2.5 \times 10^5$ pfu of s51 or mock infected with diluent alone and sacrificed at 24 or 48 hours post infection. At the time of sacrifice, mice were perfused with 4% paraformaldehyde in PBS (pH 7.4) prior to decalcification and in situ hybridization. Paraffin embedded limb sections were probed using either a riboprobe complementary for S.A.AR86 nucleotides 7371 to 7816 or a control riboprobe specific for the influenza strain PR/8 hemagglutinin as described previously (Heise et al., (2000) *J. Virol.* 74:4207). S.A.AR86 specific in situ signal was observed in the periosteum and tendons of the long bones adjacent to the joints in mice infected with either dose of virus. Consistent with virus titration results (FIG. 1A), S.A.AR86 specific in situ signal was rarely found in muscle tissue. Replication was also restricted to the epiphyses (ends) of the long bones, adjacent to the joints, while in situ signal was not observed in the diaphyses of the long bones. Specific signal was not observed in periosteum or tendons from mock infected mice probed with the S.A.AR86 specific riboprobe or in tissues from infected mice probed with the influenza HA specific riboprobe (FIG. 2 and data not shown). Similar results were observed following in situ hybridization of limb sections from mice infected with s51 by the intracranial route (data not shown). Although in situ signal was not observed within the joint synovium, signal was observed in periosteum and tendons immediately adjacent to the synovial cavity (FIG. 2D). In addition to the periosteum and tendons, in situ signal was observed in the endosteum within the epiphyses of the long bones (data not shown). However, since this signal involved single infected cells, and the smaller spaces within the marrow cavities might lead to non-specific probe binding, we were interested in confirming that the endosteum was truly a site of viral replicon.

EXAMPLE 4

To confirm the in situ hybridization results, mice were infected with S.A.AR86 based vectors driving expression of green fluorescent protein (GFP). GFP expression provides a sensitive method of detecting infected cells both in vivo and in vitro (Valdivia et al., (1996) *Gene* 173:47). GFP is extremely stable, tolerates the decalcification conditions used in making sections from bone/joint tissue (K. Bernard, and R. E. J., unpublished), and provides a sensitive method for detecting virally infected cells in calcified tissues.

The first type of viral vector used was a S.A.AR86 based double promoter vector, which was constructed by placing a second S.A.AR86 subgenomic promoter immediately upstream of the s55 3' untranslated region, as described previously for other alphaviruses (reviewed in Frolov et al., (1996) *Proc. Natl. Acad. Sci. U. S. A.* 93:11371). This virus, s55-gfp(F), expressed the mut2 GFP gene (kindly provided by Stanley Falkow, Stanford University). The original GFP gene was subsequently replaced with the enhanced green fluorescent protein (Egfp; Clonetech, Palo Alto, Calif.) to create the clone, ps55-gfp. This double promoter virus was placed on the s51 background to create clone ps51-gfp. Clone ps51-gfp has a single coding change (nsP1 538 Thr to Ile), which resulted in a 5–10 fold increase in GFP expression in BHK-21 cells compared to ps55-gfp (M. T. H., D. A. S, and R. E. J. unpublished). GFP expression by the viruses was stable in vivo, since 100% of plaques isolated from bone/joint tissue at 3 days post-infection were GFP positive (data not shown).

Figure 3:
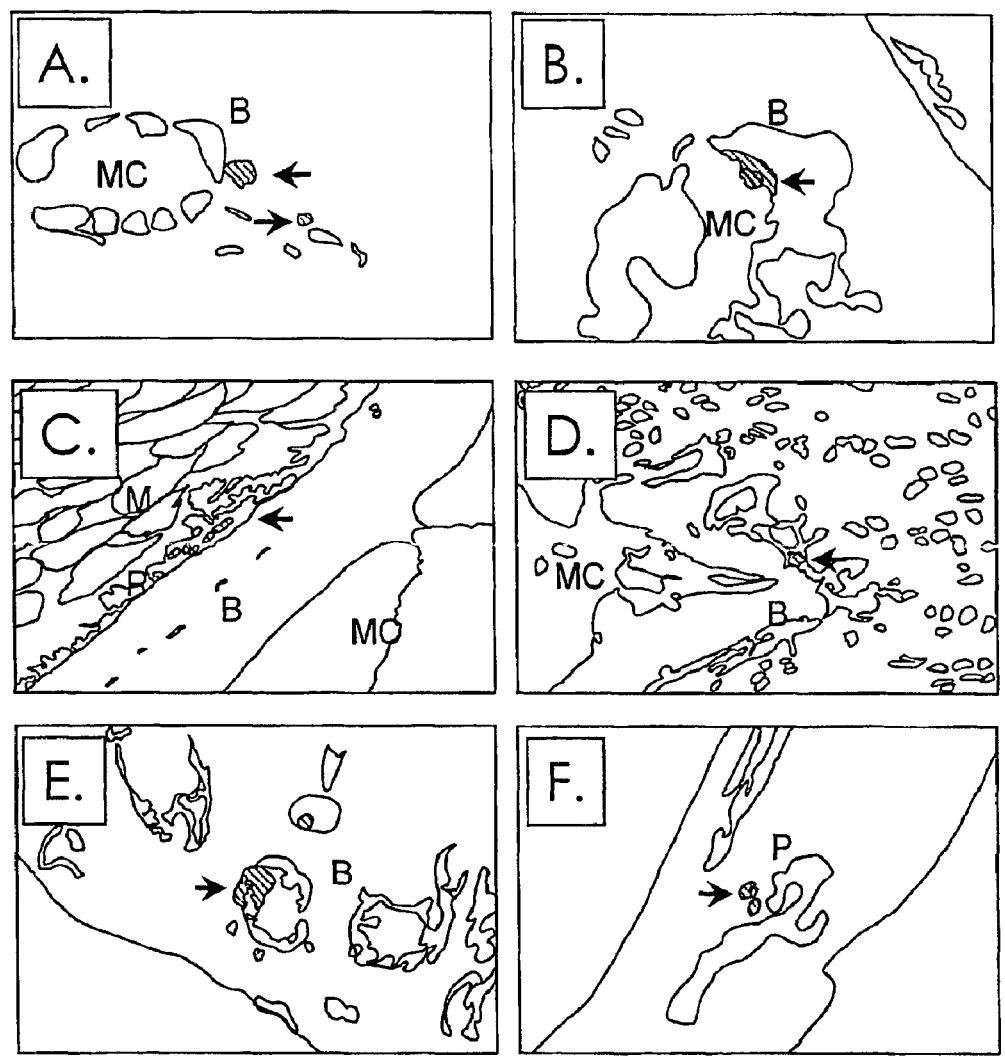
FIG. 3. S.A.AR86-based double promoter viruses and replicons infect cells within the endosteum and periosteum. Four week old female CD-1 mice were infected iv with $10^3$ pfu of the double promoter virus s55-gfp(F), 1.5×10⁶ pfu of the double promoter virus s51-gfp or 2×10⁶ iu of the replicon REP91-gfp. Mock infected mice received PBS diluent alone. Mice infected with the $10^3$ dose of s55-gfp(F) were sacrificed three days post infection, while mice receiving high doses of s51-gfp or replicon were sacrificed at 12–14 hours post infection. Following sacrifice, mice were perfused with 4% paraformaldehyde, and hind limbs were decalcified before preparation of frozen sections. GFP positive cells were visualized by fluorescent microscopy. Panels A and B=$10^3$ pfu of s55-gfp(F), panels C and D=1.5×10⁶ pfu of s51-gfp, and panels E and F=REP91-gfp. Panels A and B: GFP positive cells within the endosteum of a s55-gfp(F) infected mouse. 600× magnification, triple pass FITC/Texas Red filter. Panel C: GFP positive cells within the periosteum of a mouse infected with 1.5×10⁶ pfu of s51-gfp. Red staining indicates the presence of type I collagen in calcified tissue, which was identified using anti-mouse type I collagen (Rockland). 400× magnification, triple pass FITC/Texas Red filter. Panel D: GFP positive cell adjacent to calcified tissue in a s51-gfp infected mouse, 400× magnification, FITC filter. Panel E. GFP positive cell within the endosteum of REP91-gfp infected mouse, 400× magnification, Triple pass FITC/Texas Red filter. Panel F: GFP positive cells within the periosteum of a REP91-gfp infected mouse, 400× magnification, Triple pass FITC/Texas Red filter. Tissue types are designated by the following abbreviations within the figures: B=bone, M=muscle, P=periosteum, and mc=marrow cavity.

Adult CD-1 mice were infected iv with $10^3$ pfu or $1–3 \times 10^6$ pfu of GFP expressing double promoter virus. The $10^3$ dose was chosen for direct comparison to studies with s55 or s51 infection (FIG. 1). However, the double promoter viruses were attenuated for replication in vivo compared to wild-type s55 and s51. Following infection with $10^3$ pfu of s51-gfp or s51, the double promoter virus produced titers within the femur/knee joint that were 10 fold lower than s51 at 24 hours post infection. When the dose of s51-gfp was increased to $10^6$ pfu, viral titers within the femur were equal to or higher than those observed following infection with $10^3$ pfu of s51 (data not shown). Therefore, additional experiments were performed in which 4 week old female CD-1 mice were infected with $1–3 \times 10^6$ pfu of s51-gfp iv. Since both s55 and s51 replicate equally well in bone/joint tissue (FIG. 1), most in vivo experiments were performed using s51-gfp due to its higher level of GFP expression. However, initial studies using the $10^3$ dose were performed with clone ps55-gfp(F). Mice were sacrificed at 12 to 14 hours or 3 days post infection, exsanguinated, and perfused with 4% paraformaldehyde in PBS (pH. 7.3), and hind limbs were decalcified. Frozen sections were then prepared from the decalcified hind limbs. GFP positive cells were observed within hind limb sections from animals that received either low doses of s55-gfp(F) or high doses of s51-gfp, but not in mock infected animals. GFP positive cells localized to the same areas with either dose of virus, though more GFP positive cells were observed with the high dose. Consistent with the in situ hybridization studies, GFP positive cells localized to bone-associated connective tissue following infection with either low (FIGS. 3A and B) or high doses (FIGS. 3C and D) of double promoter virus. Furthermore, the GFP positive cells localized to both the endosteum and periosteum of the epiphyses of the long bones adjacent to the joints. The periosteum was a major site of infection with clusters of GFP positive cells readily observable adjacent to bone (FIG. 3C).

EXAMPLE 5

In addition to double promoter viruses, S.A.AR86 based replicons expressing GFP were used to identify sites of S.A.AR86 infection within bone and or joint tissue. Alphavirus-derived replicon RNA is packaged with the viral structural proteins provided in trans by helper RNAs. This results in the production of replicon particles that exhibit the same coat proteins as the parental virus, but are able to undergo only a single round of replication (reviewed in Frolov et al., (1996) *Proc. Natl. Acad. Sci. U. S. A.* 93:11371). Therefore, GFP expression by the replicon can be used to identify the initial cellular targets of viral replication within a given tissue. A S.A.AR86 based replicon containing the s51 nonstructural genes and driving expression of GFP in place of the viral structural genes was constructed and designated REP91-gfp. A glycoprotein helper plasmid was engineered to produce a helper RNA containing the S.A.AR86 26S subgenomic promoter driving expression of a fusion protein consisting of the first 74 amino acids of capsid, a 2 amino acid linker, 17 amino acids of the foot and mouth disease virus 2A (FMDV2A) protease (Matton et al., (1996) *J. Virol.* 70), and the viral glycoproteins. The capsid RNA sequence permits efficient translation of the fusion protein, while the FMDV2A protease cleaves itself and the capsid fragment from the E3 glycoprotein to allow glycoprotein maturation. The capsid helper was similar to those described for other alphavirus replicon packaging systems (reviewed in Frolov et al., (1996) *Proc. Natl. Acad. Sci. U. S. A.* 93:11371). In vitro transcribed RNA from pREP91-gfp, the capsid helper (pCAP86), and the glycoprotein helper (pHelp102) was prepared using mMessage mMachine SP6 in vitro transcription kits (Ambion; Austin, Tex.) and introduced into BHK-21 cells by electroporation (Pushko et al., (1997) *Virol. 239:389*). Before the replicon stocks were used in vivo, they were evaluated by serial passage of 10 to 20% of the replicon stock on BHK-21 cells that were examined for cytopathic effect from propagation competent recombinant virus. If free of cpe after two passages, replicon particle stocks were considered to be usable for experimental purposes.

Mice were infected iv with $1-2 \times 10^6$ infectious units (iu) of REP91-gfp. Since, REP91-gfp is able to undergo only a single round of replication, high doses of replicon particles were required for delivery to bone and/or joint tissue. Following inoculation, mice were sacrificed 12–14 hours post infection and frozen sections prepared as with the double promoter viruses. Results with replicons were identical to those seen with the double promoter viruses s55-gfp(F), s55-gfp, or s51-gfp. REP91-gfp infected cells were localized to the endosteum and periosteum, near the ends of the femur and tibia (FIG. 3E and F). Seventy-eight sagittal sections from the fore and hind limbs of replicon infected mice were screened for GFP positive cells. These sections included representative areas of the diaphysis, epiphyses, joints, and surrounding muscle tissue. This screen identified 55 cells that were GFP positive, 46 of which were located in the epiphyses of the long bones. Of these 46 GFP positive cells, 13 were found in the endosteum and 33 in the periosteum. Of the GFP positive cells not clearly located in the epiphyses, all 9 were located in the periosteum or endosteum. Two GFP positive cells were located in the periosteum of the diaphysis and it was unclear whether the other 7 cells were located in the diaphysis or epiphysis. No GFP positive cells were found in muscle tissue, in synovial cells, or in bone marrow not intimately associated with calcified tissue. These results, in combination with the in situ hybridization results from FIG. 2 clearly demonstrate that in an adult mouse model, an alphavirus associated with arthralgia in humans exhibits tropism for bone associated connective tissue and that the predominant site of replication is the epiphyses adjacent to the joints.

EXAMPLE 6

Figure 4:
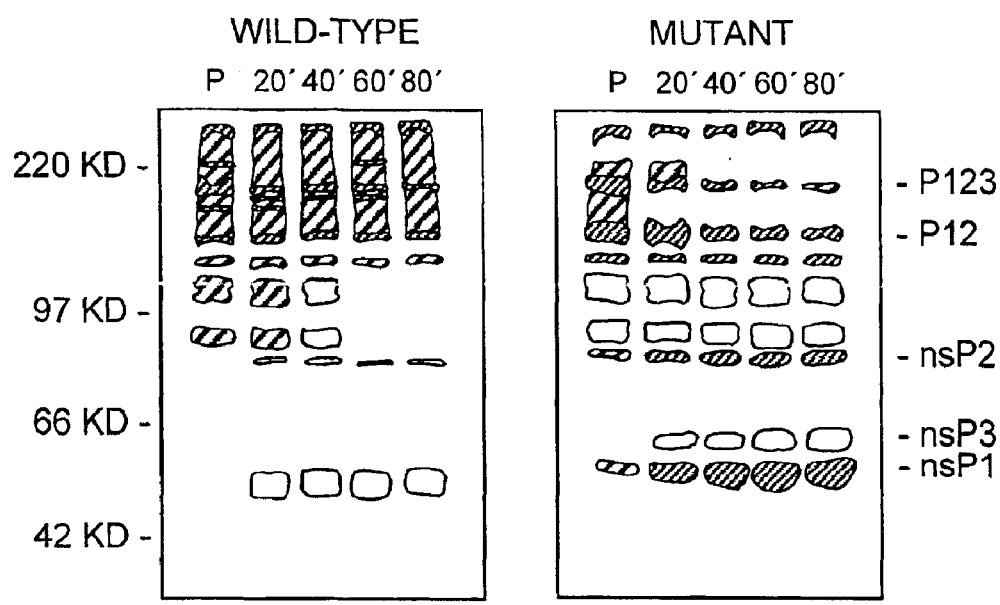
FIG. 4. In vitro translation reactions were performed using rabbit reticulocyte lysates to translate full length s55 (nsP1 538 Thr) and s51 (nsP1 538 Ile) RNAs. The translation reactions were performed in the presence of $^{35}$S methionine so that the full-length translation products and their cleavage products could be visualized by gel electrophoresis. Following the initial radioactive pulse, the reactions were chased with excess nonradioactive methionine and cycloheximide to stop new protein synthesis. Left panel: s55. Right panel: s51.

In vitro translation reactions were performed using rabbit reticulocyte lysates to translate full length s55 (nsP1 538 Thr) and s51 (nsP1 538 Ile) RNAs. The translation reactions were performed in the presence of $^{35}$S methionine so that the full length translation products and their cleavage products could be visualized by gel electrophoresis. Following the initial radioactive pulse, the reactions were chased with excess nonradioactive methionine and cycloheximide to stop new protein synthesis. This allowed evaluation of the kinetics of nonstructural protein processing since the protease encoded by nsP2 is active in the translation reactions. Using this procedure it was found that the nonstructural protein precursors (P123) and the cleavage intermediate (P12) were more stable for the nonstructural proteins containing threonine at nsP1 538 (FIG. 4, left panel). In contrast, the presence of isoleucine at nsP1 538 resulted in the rapid disappearance of P123 and P12 and the accumulation of mature nsP1 and nsP2 (FIG. 4, right panel). These results are consistent with the hypothesis that the attenuating isoleucine accelerates processing of the viral nonstructural proteins.

EXAMPLE 7

Figure 5:
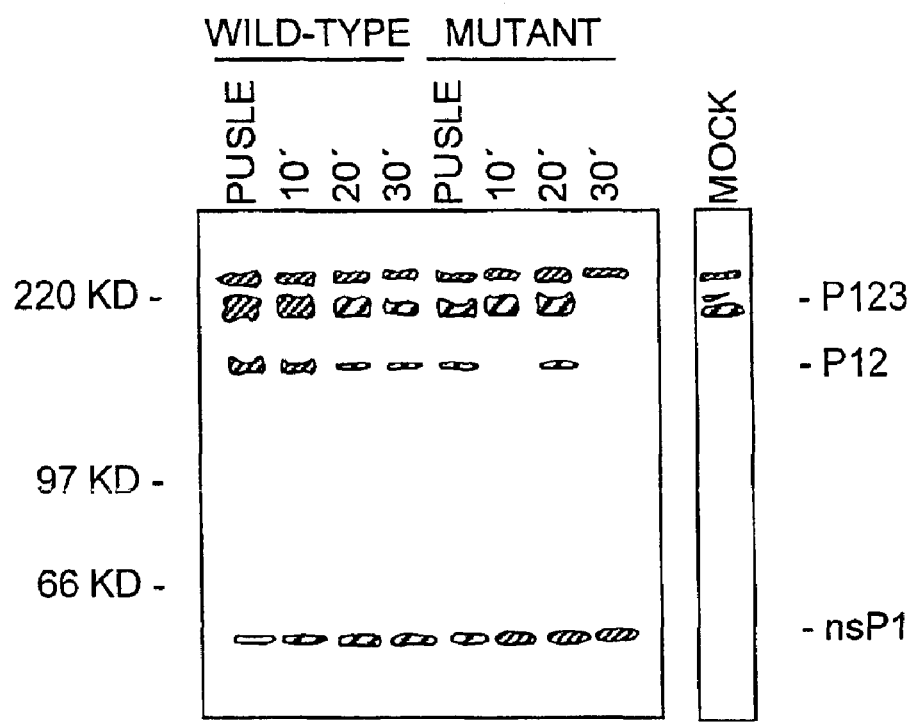
FIG. 5. BHK-21 cells were infected with s55 (Thr) or s51 (Ile) at a multiplicity of infection of 5.0. Cells were labeled with $^{35}$S methionine and then chased with an excess of cold methionine to measure the rate of nonstructural protein cleavage. At various times in the pulse/chase, cell lysates were generated and nsP1 was immunoprecipitated using protein specific antibodies. The radioactive proteins were visualized by gel electrophoresis and autoradiography.

BHK-21 cells were infected with s55 (Thr) or s51 (Ile) at a multiplicity of infection of 5.0. Cells were labeled with $^{35}$S methionine and then chased with an excess of cold methionine to measure the rate of nonstructural protein cleavage. At various times in the pulse/chase, cell lysates were generated and nsP1 was immunoprecipitated using protein specific antibodies. The radioactive proteins were visualized by gel electrophoresis and autoradiography. As shown in FIG. 5, the attenuated s51 virus exhibited a more rapid accumulation of mature nsP1 and loss of the P123 precursor and P12 cleavage intermediate compared to the s55 virus, which showed delayed accumulation of mature nsP1 and greater stability of the P123 and P12 precursor proteins.

The results shown in FIG. 4 and FIG. 5 demonstrate that the attenuating mutations at nsP1 538 (Thr→Ile) accelerates the processing of the viral nonstructural proteins, resulting in the more rapid accumulation of mature nonstructural proteins in cells infected with the mutant virus.

EXAMPLE 8

Figure 6:
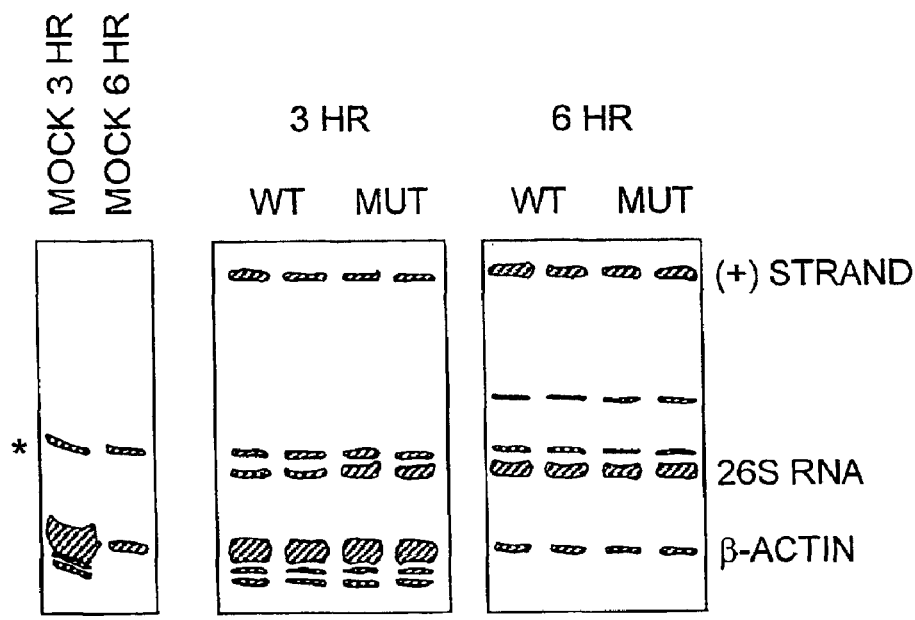
FIG. 6. BHK-21 cells were infected with s55 (nsP1 538 Thr) or s51 (nsP1 538 Ile) at a multiplicity of infection (MOI) of 5.0. Infection was allowed to go for one hour before washing the cells 3 times with room temperature PBS (1% DCS and Ca$^{++}$/Mg$^{++}$). Cells were then incubated in growth media until time of RNA harvest. At 3 and 6 hours post infection, the dishes were transferred to ice and total cellular RNA was harvested. RNAse protection assays were performed to detect the viral 26S and plus strand RNAs (Panel A) or the minus strand RNA (Panel B). A probe specific for mouse β-actin was used to control for RNA loading.
Figure 6:
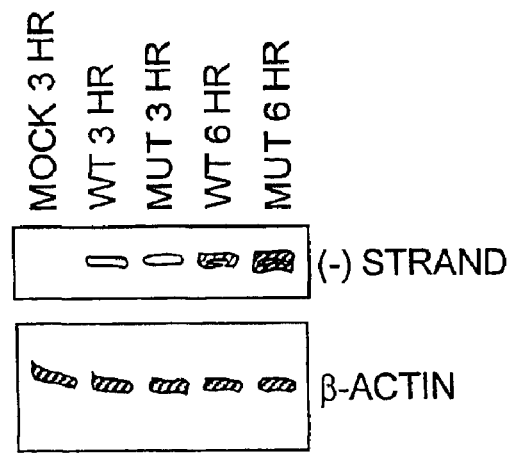

BHK-21 cells were infected with s55 (nsP1 538 Thr) or s51 (nsP1 538 Ile) at a multiplicity of infection (MOI) of 5.0. Infection was allowed to go for one hour before washing the cells 3 times with room temperature PBS (1% DCS and $Ca^{++}/Mg^{++}$). Cells were then incubated in growth media until time of RNA harvest. At 3 and 6 hours post infection, the dishes were transferred to ice and total cellular RNA was harvested. RNAse protection assays were performed to detect the viral 26S and Plus strand RNAs (FIG. 6, Panel A) or the minus strand RNA (FIG. 6, panel B). A probe specific for mouse β-actin was used to control for RNA loading. The attenuated s51 virus exhibited a consistent 3–4 fold increase in 26S RNA levels compared to the wild type virus at 3 hours post infection. No difference was observed for plus and minus strand RNAs. The levels of 26S RNA were equivalent for the two viruses at 6 hours post infection, indicating that the effect of Ile at nsP1 538 was transient.

EXAMPLE 9

BHK-21 cells were inoculated with S.A.AR86 derived replicon particles with the wild type Thr or the attenuating Ile at nsP1 position 538. These replicons expressed green fluorescent protein (GFP) from their 26S promoters, which allowed analysis of GFP expression as a readout for 26S promoter expression. Infections were performed at a multiplicity of infection of 0.1 and cells were analyzed by flow cytometry to measure of GFP fluorescence at 4 hours post infection. Cells inoculated with the Ile containing replicon expressed GFP at 5–10 fold higher levels than the wild type Thr containing replicon at 4 hours post infection (FIG. 7).

Figure 7:
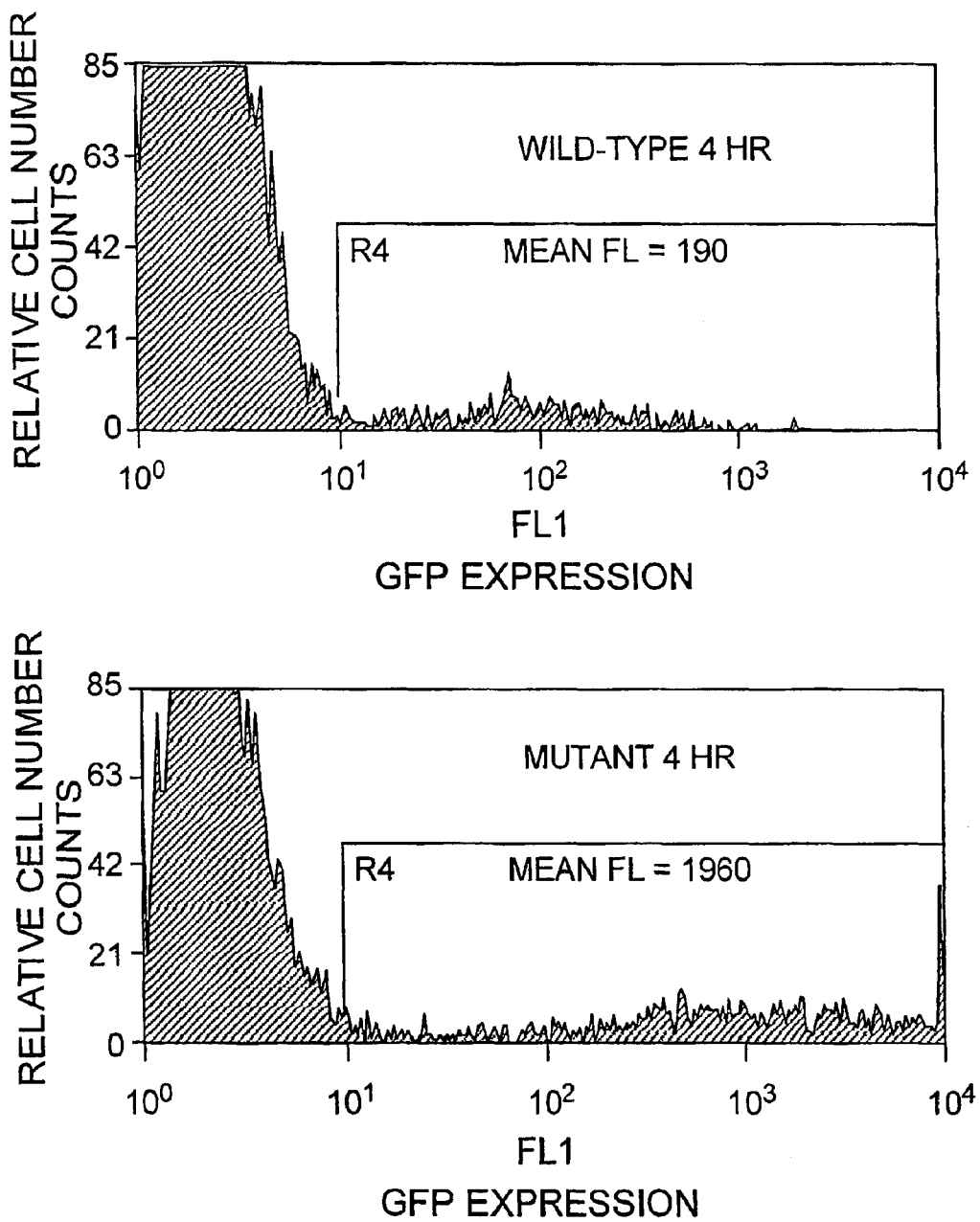
FIG. 7. BHK-21 cells were inoculated with S.A.AR86 derived replicon particles with the wild type Thr or the attenuating Ile at nsP1 position 538. These replicons expressed green fluorescent protein (GFP) from their 26S promoters, which allowed analysis of GFP expression as a readout for 26S promoter expression. Infections were performed at a multiplicity of infection of 0.1 and cells were analyzed by flow cytometry to measure of GFP fluorescence at 4 hours post infection.

FIG. 6 and FIG. 7 demonstrate that the attenuating mutations at nsP1 538 (Thr→Ile) resulted in more rapid and increased expression from the viral 26S promoter.

Therefore, the attenuating mutation would be expected to increase the safety of S.A.AR86 derived replicons while actually increasing production of the heterologous gene from the 26S promoter. This increased expression may enhance the ability of these vectors to induce a strong immune response against the heterologous gene.

EXAMPLE 10

A second mutation, at nsP3 position 537 (cysteine to opal termination codon) also attenuated S.A.AR86 for neurovirulence without affecting viral growth in cell culture or expression from the viral 26S promoter. Viruses containing a Thr→Ile attenuating mutation at nsP1 538, or a Cys→opal attenuating mutation at nsP3 537, or both mutations were generated. Viruses were administered to 6 week old CD-1 mice via the intracranial route and animals were evaluated for virus induced morbidity and mortality. The nsP1 538 mutation (Ile) alone caused moderate paresis in 100 percent of infected animals, but little to no mortality. The nsP3 537 mutation caused moderate to severe paresis in 75% of infected animals and 50% mortality. A virus with both mutations caused no mortality and transient mild hind limb paresis in 75% of infected animals, and transient moderate paresis in 25% of infected animals. In direct comparisons, the clinical scores for mice infected with the nsP1 538 mutant were always higher and the disease signs lasted longer than for mice infected with the double mutant.

The combination of the nsP3 537 and nsP1 538 mutations is additive, resulting in a virus that is extremely attenuated for adult mouse neurovirulence. Therefore, we are able to increase the safety of S.A.AR86 derived vectors, while actually increasing expression of the heterologous gene (due to Ile at nsP1 538), which may increase the effectiveness of these vectors as vaccine delivery vehicles.

EXAMPLE 11

Figure 8:
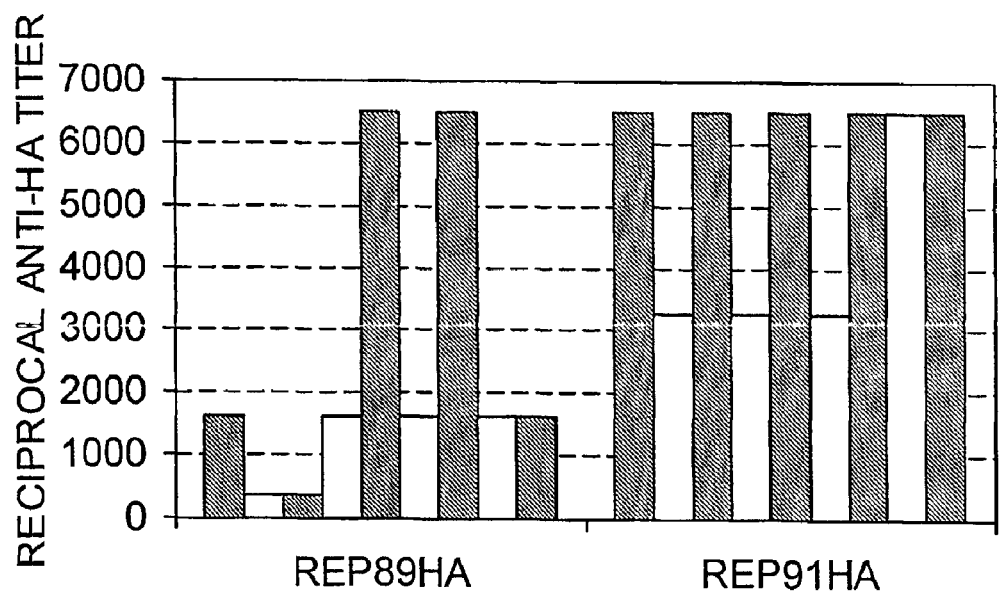
FIG. 8. Female CD-1 mice were immunized with $10^4$ infectious Units of REP89HA (nsP1 538 Thr) or REP91HA (nsP1 538 Ile). Serum from the inoculated mice was evaluated for anti-influenza virus hemagglutinin (HA) antibody at 12 weeks post inoculation using an ELISA specific for influenza virus HA. Results are shown as the reciprocal of the last dilution positive for anti-HA antibody. These results demonstrate that the presence of Ile at nsP1 538 results in consistently higher serum anti-HA antibody responses in the immunized mice compared to mice immunized with the wild type REP89HA replicon containing Thr at nsP1 538. Female CD-1 mice were immunized with $10^4$ infectious Units of REP89HA (nsP1 538 Thr) or REP91HA (nsP1 538 Ile). Serum from the inoculated mice was evaluated for anti-influenza virus hemagglutinin (HA) antibody at 12 weeks post inoculation using an ELISA specific for influenza virus HA. Results are shown as the reciprocal of the last dilution positive for anti-HA antibody. These results demonstrate that the presence of Ile at nsP1 538 results in consistently higher serum anti-HA antibody responses in the immunized mice compared to mice immunized with the wild type REP89HA replicon containing Thr at nsP1 538.

Four to Six week old CD-1 mice were inoculated subcutaneously in the left rear footpad with $10^4$ infectious units (iu) of S.A.AR86 replicon expressing the hemagglutinin (HA) of influenza virus. Replicons contained either Ile (REP91 HA) or Thr (REP89HA) at nsP1 538. Serum was harvested from the immunized mice at 12 weeks post inoculation and evaluated for anti-HA antibody using a HA specific ELISA. Both replicons elicited an anti-HA response, however, the level of anti-HA response was consistently higher in animals immunized with REP91 HA (FIG. 8).

Additional studies were performed to directly assess the ability of REP91HA versus REP89HA to induce antibody responses. Adult CD-1 mice were inoculated with $10^4$ iu of REP91 HA or REP89HA. Twelve weeks after the initial inoculation, mice were boosted with $10^4$ iu of REP91 HA or REP89HA. Mice were sacrificed 10 days post boost and the number of antigen specific antibody secreting cells in the spleen was evaluated using a HA specific elispot assay. REP89HA (nsP1 538 Thr) immunization induced an average of 2.8+/−2.2 HA specific antibody cells per $10^5$ spleen cells. In contrast, REP91HA (nsP1 538 Ile) induced 34.8+/−17 HA specific antibody secreting cells per $10^5$ spleen cells. So immunization with a replicon encoding Ile at nsP1 position 538 resulted in an increase of approximately 12 fold in the number of antigen specific antibody secreting cells compared to mice immunized with the wild type S.A.AR86 replicon encoding Thr at nsP1 position 538. This data demonstrates that in addition to increasing the safety of S.A.AR86 based vectors by attenuating S.A.AR86 for adult mouse neurovirulence, the presence of Ile at nsP1 position 538 also enhances the humoral immune response generated against the heterologous gene encoded by the S.A.AR86 vector.

Although the foregoing invention has been described in some detail by way of illustration and example for purposes of clarity and understanding, it will be obvious that certain changes and modifications may be practiced within the scope of the appended claims and equivalents thereof.

---

---

What is claimed is:

1. A South African Arbovirus No. 86 (S.A.AR86) genomic RNA, said S.A.AR86 genomic RNA comprising:
   (a) S.A.AR86 nonstructural protein (nsp) and/or S.A.AR86 structural protein coding sequences, wherein the S.A.AR86 nonstructural protein and/or structural protein coding sequences encode an attenuating mutation selected from the group consisting of:
      (i) an attenuating mutation in the cleavage domain between the nsp1 and nsp2 coding sequences;
      (ii) an attenuating mutation that results in a termination codon at nsp3 amino acid position 537,
      (iii) an attenuating mutation comprising a substitution mutation at nsp3 amino acid position 385,
      (iv) an attenuating mutation comprising an insertion of at least 8 amino acids following nsp3 amino acid position 385,
      (v) an attenuating mutation comprising a substitution at E2 amino acid position 243, and (vi) a combination of the attenuating mutations of (i) to (v)

(b) a heterologous nucleotide sequence; and (c) an alphavirus capsid enhancer sequence operatively associated with said heterologous nucleotide sequence.

2. The genomic RNA of claim 1, wherein said genomic RNA further comprises a promoter that is operatively associated with said heterologous nucleotide sequence.

3. The genomic RNA of claim 1, wherein said genomic RNA comprises an attenuating mutation in the cleavage domain between the nsp1 and nsp2 coding sequences comprising a substitution mutation at nsP1 amino acid position 538.

4. The genomic RNA of claim 1, wherein said genomic RNA comprises an attenuating mutation that results in an opal termination codon at nsp3 amino acid position 537.

5. The genomic RNA of claim 1, wherein said genomic RNA comprises an attenuating mutation comprising:

(a) a substitution mutation at nsP3 amino acid position 385, and (b) insertion of the amino acid sequence of SEQ ID NO:1 or at least 8 contiguous amino acids of SEQ ID NO:1 following nsp3 amino acid position 385.

6. The genomic RNA of claim 1, wherein said genomic RNA expresses a fusion protein comprising a polypeptide encoded by said heterologous nucleotide sequence and a polypeptide encoded by said capsid enhancer sequence.

7. The genomic RNA of claim 1, wherein said genomic RNA further comprises a segment encoding an exogenous protease.

8. The genomic RNA of claim 7, wherein said genomic RNA expresses a fusion protein comprising a polypeptide encoded by said heterologous nucleotide sequence, the exogenous protease, and a polypeptide encoded by said capsid enhancer sequence.

9. The genomic RNA of claim 7, wherein said genomic RNA comprises, in the 5' to 3' direction, said alphavirus capsid enhancer sequence, said segment encoding said exogenous protease, and said heterologous nucleotide sequence.

10. The genomic RNA of claim 1, wherein said capsid enhancer sequence comprises a coding sequence for an amino terminal portion of an alphavirus capsid protein.

11. The genomic RNA of claim 1, wherein said capsid enhancer sequence is a S.A.AR86 capsid enhancer sequence.

12. The genomic RNA of claim 1, wherein said genomic RNA is a replicon molecule that does not express at least one of the S.A.AR86 structural proteins.

13. The genomic RNA of claim 1, wherein said genomic RNA is a replicon molecule that does not express a S.A.AR86 E1 glycoprotein, a S.A.AR86 E2 glycoprotein, or both.

14. The genomic RNA of claim 1, wherein said S.A.AR86 genomic RNA is a replicon molecule that does not express a S.A.AR86 capsid protein.

15. The genomic RNA of claim 1, wherein said genomic RNA is a replicon molecule that does not express any of the S.A.AR86 structural proteins.

16. The genomic RNA of claim 15, wherein the sequences encoding the non-expressed S.A.AR86 structural protein(s) have been deleted from the replicon molecule.

17. The genomic RNA of claim 1, wherein said heterologous nucleotide sequence encodes a polypeptide.

18. The genomic RNA of claim 17, wherein said heterologous nucleotide sequence encodes an immunogenic polypeptide.

19. An infectious alphavirus particle comprising:

(a) alphavirus structural proteins, (b) the S.A.AR86 genomic RNA of claim 1 packaged within the assembled alphavirus structural proteins of (a).

20. The alphavirus particle of claim 19, wherein said alphavirus structural proteins are S.A.AR86 structural proteins.

21. An infectious, defective alphavirus particle comprising:

(a) alphavirus structural proteins, (b) the S.A.AR86 genomic RNA of claim 12 packaged within the assembled alphavirus structural proteins of (a).

22. A composition comprising a plurality of alphavirus particles according to claim 19.

23. A pharmaceutical formulation comprising an immunogenic amount of the alphavirus particles of claim 19 in a pharmaceutically acceptable carrier, wherein said heterologous nucleotide sequence encodes an immunogenic polypeptide.

24. A method of producing an immune response in a subject, comprising:

administering to the subject the pharmaceutical formulation of claim 23;

wherein the composition is administered in an amount and under conditions such that an immune response is produced against the immunogenic polypeptide in the subject.

25. A helper cell for packaging alphavirus particles, comprising in an alphavirus-permissive cell:

(a) a S.A.AR86 replicon RNA according to claim 12, (b) one or more helper sequences encoding at least the alphavirus structural proteins that are not encoded by said replicon RNA.

26. The helper cell of claim 25, wherein said alphavirus structural proteins are S.A.AR86 structural proteins.

27. The helper cell of claim 25, wherein said one or more helper sequences only encode the alphavirus structural proteins that are not provided by the replicon RNA.

28. The helper cell of claim 25 wherein at least one of said helper sequence(s) is stably incorporated into the genome of said helper cell.

29. The helper cell of claim 25 wherein at least one of said helper sequences(s) is a plasmid.

30. The helper cell of claim 25, wherein said replicon RNA is expressed from a DNA sequence that has been introduced into said helper cell.

31. The helper cell of claim 30, wherein said DNA sequence is stably incorporated into the genome of said helper cell.

32. The helper cell of claim 30, wherein said DNA sequence is a plasmid or a viral vector.

33. The helper cell of claim 25, wherein (a) said replicon RNA is introduced into said helper cell by electroporation, or (b) said helper sequences are RNA sequences that are introduced into the helper cell by electroporation, or (c) both (a) and (b).

34. The helper cell of claim 25, wherein said helper sequences lack an alphavirus packaging sequence.

35. The helper cell of claim 25, wherein said heterologous nucleotide sequence encodes a polypeptide.

36. The helper cell of claim 35, wherein said heterologous nucleotide sequence encodes an immunogenic polypeptide.

37. A method of making an infectious, defective alphavirus particle, comprising:
  (a) providing a helper cell according to claim 25 under conditions sufficient to produce alphavirus particles in the helper cell,
  (b) producing alphavirus particles in the helper cell, and
  (c) collecting the alphavirus particles produced by the helper cell;
  wherein the combined expression of the S.A.AR86 replicon RNA and the helper sequence(s) produces an assembled alphavirus particle comprising the S.A.AR86 replicon RNA packaged within the alphavirus structural proteins, and further wherein said assembled alphavirus particle is able to infect an alphavirus-permissive cell but is unable to propagate by producing new alphavirus particles in the cell in the absence of helper sequences.

38. A composition comprising a plurality of infectious, defective alphavirus particles produced according to claim 37.

39. A DNA molecule comprising:
  (a) a segment encoding a S.A.AR86 genomic RNA according to claim 1, and
  (b) a promoter operatively associated with said segment encoding said S.A.AR86 genomic RNA.

40. An infectious RNA transcript encoded by the DNA molecule of claim 39.

41. A vector comprising the DNA molecule of claim 39.

42. A cell comprising the vector of claim 41.

43. A composition comprising a plurality of alphavirus particles according to claim 21.

44. A pharmaceutical formulation comprising an immunogenic amount of the alphavirus particles of claim 21 in a pharmaceutically acceptable carrier, wherein said heterologous nucleotide sequence encodes an immunogenic polypeptide.

45. A method of producing an immune response in a subject, comprising;
  administering to the subject the pharmaceutically formulation of claim 44;
  wherein the composition is administered in an amount and under conditions such that an immune response is produced against the immunogenic polypeptide in the subject.

46. The genomic RNA of claim 1, wherein said genomic RNA comprises an attenuating mutation comprising a substitution at E2 amino acid position 243.

47. An infectious alphavirus particle comprising:
  (a) alphavirus structural proteins comprising a S.A.AR86 E2 glycoprotein comprising an attenuating mutation comprising a substitution at E2 amino acid position 243,
  (b) an alphavirus genomic RNA packaged within the assembled alphavirus structural proteins of (a).

48. The genomic RNA of claim 1, wherein the genomic RNA comprises attenuating mutations comprising:
  (a) an attenuating mutation comprising a substitution at nsp1 amino acid position 538;
  (b) an attenuating mutation that results in a termination codon at nsp3 amino acid position 537;
  (c) an attenuating mutation comprising insertion of the amino acid sequence of SEQ ID NO:1 or at least 8 continuous amino acids of SEQ ID NO:1 following nsp3 amino acid position 385; and
  (d) an attenuating mutation comprising a substitution at E2 position amino acid position 243.

* * * * *